ary Examiner—Robert Gerstl

United States Patent [19]

Hay et al.

[11] Patent Number: 4,521,241
[45] Date of Patent: Jun. 4, 1985

[54] HERBICIDAL BENZENESULFONAMIDES

[75] Inventors: James V. Hay, Newark; Richard F. Sauers, Hockessin, both of Del.

[73] Assignee: E. I. Du Pont de Nemours and Company, Wilmington, Del.

[21] Appl. No.: 533,773

[22] Filed: Sep. 19, 1983

[51] Int. Cl.$^3$ .................. C07D 409/12; C07D 405/12; C07D 401/12; A01N 47/36
[52] U.S. Cl. ............................................ 71/92; 71/90; 71/93; 544/209; 544/212; 544/321; 544/322; 544/323; 544/331; 544/332
[58] Field of Search ...................... 71/90, 92; 544/321, 544/322, 323, 331, 332

[56] References Cited

FOREIGN PATENT DOCUMENTS 0079683 5/1983 European Pat. Off. ................ 71/92
0099339 1/1984 European Pat. Off. ................ 71/92

Primary Examiner—Robert Gerstl

[57] ABSTRACT

Sulfonylurea compounds which contain dihydroisobenzofuran, dihydroisobenzothiophene, or isoindoline 4-sulfonamide substituents such as 1,3-dihydro-N-[(4-methoxy-6-methylpyrimidin-2-yl)aminocarbonyl]benzo[c]furan-4-sulfonamide and their use as agricultural chemicals, including plant growth regulants and herbicides.

18 Claims, No Drawings

HERBICIDAL BENZENESULFONAMIDES

BACKGROUND OF THE INVENTION

This invention relates to novel sulfonylurea compounds and their use as agricultural chemicals, including plant growth regulants and herbicides.

U.S. Pat. Nos. 4,127,405, issued Nov. 28, 1978, and 4,169,719, issued Oct. 2, 1979, both patents to Levitt, disclose N-[(1,3,5-triazin-2-yl)aminocarbonyl]arylsulfonamides and N-(heterocyclicaminocarbonyl)arylsulfonamides, respectively, which are useful as agricultural chemicals.

U.S. Pat. No. 4,348,220, issued Sept. 7, 1982 to Schwing discloses sulfonylurea compounds containing alkoxyalkyl substituents.

U.S. Ser. No. 410,993, filed Aug. 27, 1982, discloses benzofuran and benzothiophene sulfonamides which are useful as agricultural chemicals.

SUMMARY OF THE INVENTION

This invention relates to novel compounds of Formula I, suitable agricultural compositions containing them and their method-of-use as pre-emergent or post-emergent herbicides or plant growth regulants.

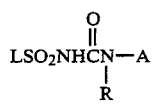

I where

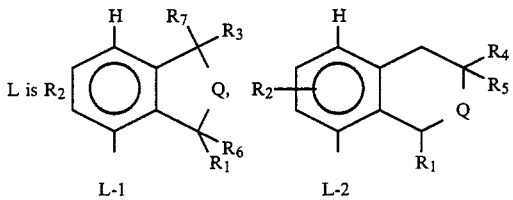

or

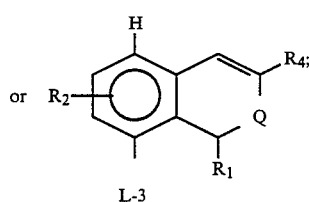

Q is O, $S(O)_n$ or $NR_3$;
n is 0, 1 or 2;
$R_1$ is H, $CH_3$, Cl or F;
$R_2$ is H, Cl, Br, $C_1-C_3$ alkoxy or $CF_3$;
$R_3$ is H or $C_1-C_4$ alkyl;
$R_4$ is H or $CH_3$;
$R_5$ is H or $CH_3$;
$R_6$ is H, Cl or F;
$R_7$ is H, Cl or F;
$R_8$ is H, Cl or F;
R is H or $CH_3$;
A is

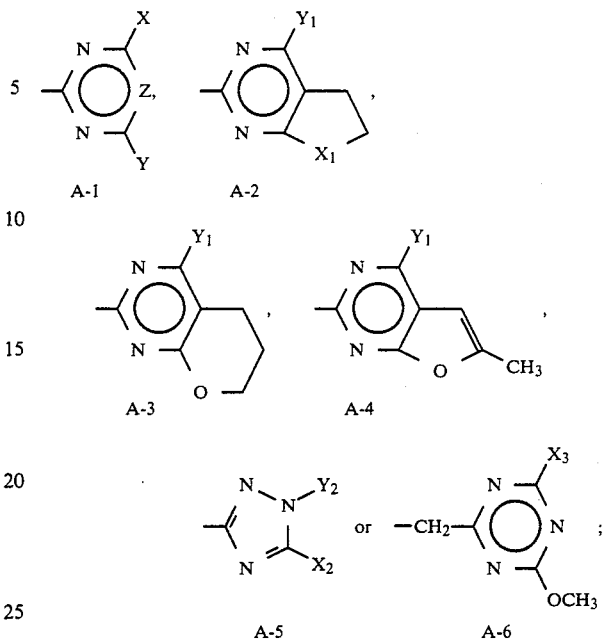

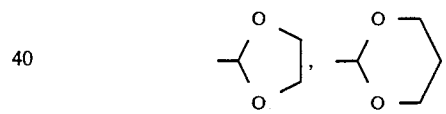

X is F, Cl, Br, $C_1-C_2$ alkyl, $C_1-C_2$ alkoxy, $OCF_2H$ or $CF_3$;
Y is H, $NH_2$, $NHCH_3$, $N(CH_3)_2$, $C_1-C_4$ alkyl, $C_1-C_4$ alkyl substituted with 1–3 atoms of (a) F, (b) Cl or (c) Br, $CH_2OCH_3$, $CH_2OC_2H_5$, $C_1-C_4$ alkoxy, $C_1-C_2$ alkylthio, $C_3-C_4$ alkenyloxy, $C_3-C_4$ alkynyloxy, $OCH_2C$-$H_2OCH_3$, $OCH_2CH_2F$, $OCH_2CH_2Cl$, $OCH_2CH_2Br$, $OCH_2CF_3$, $CH(OCH_3)_2$, $CH(OC_2H_5)_2$, or $GCF_2T$;
G is O or S;
T is H, CHClF, CHBrF, $CF_2H$ or $CHFCF_3$;
Z is CH or N;
$X_1$ is O or $CH_2$;
$Y_1$ is H, $CH_3$, $OCH_3$ or Cl;
$X_2$ is $CH_3$, $OCH_3$ or $SCH_3$;
$Y_2$ is $CH_3$, $C_2H_5$ or $CH_2CF_3$;
$X_3$ is $CH_3$ or $OCH_3$; provided that:
(1) when X is F, Cl or Br, then Z is CH and Y is $NH_2$, $NHCH_3$, $N(CH_3)_2$, $CH_3$, $OCH_3$ or $OCF_2H$; and
(2) when $R_1$ is F or Cl, when $R_6$, $R_7$ and $R_8$ are the same as $R_1$ and Q is O or S; and when $R_1$ is H or $CH_3$, then $R_6$, $R_7$ and $R_8$ are H;
and their agriculturally suitable salts.

Preferred for their higher herbicidal activity, greater plant growth regulant activity and/or more favorable ease of synthesis are:
(1) Compounds of Formula 1 where L is L-1.
(2) Compounds of Preferred 1 where A is A-1.
(3) Compounds of Preferred 2 where R is H, $R_1$ is H and $R_2$ is H.

(4) Compounds of Preferred 3 where X is Cl, CH$_3$, OCH$_3$ or OCF$_2$H and Y is CH$_3$, OCH$_3$, OCH$_2$CH$_3$, CH$_2$OCH$_3$, CH(OCH$_3$)$_2$ or GCF$_2$T where G is O and T is H.

Specifically preferred for their highest herbicidal activity, greatest plant growth regulant activity and/or more favorable ease of synthesis are the following:

1,3-Dihydro-N-[(4-methoxy-6-methylpyrimidin-2-yl)aminocarbonyl]benzo[c]furan-4-sulfonamide, m.p. 190°–194° C. (d);

1,3-Dihydro-N-[(4,6-dimethoxypyrimidin-2-yl)aminocarbonyl]benzo[c]furan-4-sulfonamide, m.p. 225°–229° C. (d);

1,3-Dihydro-N-[(4-methoxy-6-methyl-1,3,5-triazin-2-yl)aminocarbonyl]benzo[c]furan-4-sulfonamide, m.p. 199°–202° C. (d); and 1,3-Dihydro-N-[(4,6-dimethoxy-1,3,5-triazin-2-yl)aminocarbonyl]benzo[c]furan-4-sulfonamide, m.p. 202°–205° C. (d).

DETAILED DESCRIPTION OF THE INVENTION

Synthesis

The compounds of this invention of Formula I, above, there Q is O, S or SO$_2$, can be prepared, as shown in Equation 1, by reaction of the appropriate sulfonyl isocyanate of Formula II, where Q is O, S or SO$_2$, with the appropriate amine of Formula III, where R and A are as previously defined in the Summary of the Invention above.

Equation 1

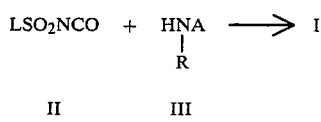

The reaction of Equation 1 is most conveniently carried out by addition of a solution of the sulfonyl isocyanate II in an inert organic solvent such as methylene chloride, acetonitrile, xylene or similar solvents to a solution or suspension of the amine III in the same solvent. Many compounds of Formula I are insoluble in the reaction solvent, and precipitate from it. They can be collected and purified by trituration with, or crystallization from, an appropriate solvent.

Those compounds of Formula I which are soluble in the reaction solvent can be isolated by evaporation of the reaction solvent followed by trituration with, or recrystallization from, an appropriate solvent.

The sulfonyl isocyanates of Formula II, where Q is O, S or SO$_2$, can be prepared from sulfonamides of Formula IV by the methods described in U.S. Pat. No. 4,379,769, issued Apr. 12, 1983 to Levitt (Equation 2).

Equation 2

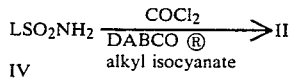

Compounds of Formula Ia, where Q is other than S(O), also can be prepared by reaction of a sulfonamide of Formula IV, where Q is other than S(O) with a carbamate of Formula V in the presence of at least one molar equivalent of trimethylaluminum.

Equation 3

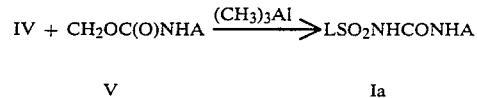

The reaction of Equation 3 is carried out by addition of trimethylaluminum to a solution or suspension of the sulfonamide of Formula IV in an inert solvent such as methylene chloride, 1,2-dichloroethane or toluene, followed by addition of the carbamate of Formula V and heating of the reaction mixture at the boiling point of the solvent for periods of about 4 to 48 hours. The compounds of Formula Ia can be isolated by the addition of dilute acid, and, if insoluble in the reaction solvent, the reaction products can be collected by filtration. If the reaction products are soluble in the reaction solvent, they can be isolated by evaporation of the solvent. Purification can be achieved by the methods described for Equation 1.

The compounds of Formula Ia where L and A are as previously defined, can also be prepared, as shown in Equation 4, by the reaction of a sulfonamide with a phenyl carbamate of Formula VI, by methods similar to those described in South African Patent Application No. 825,671.

Equation 4

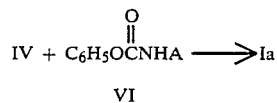

The reactants are heated together, in the presence of an inorganic or organic base, in an inert organic solvent, such as dioxane, toluene or similar solvents, for several hours. The compounds of Formula Ia can be isolated by concentration and/or evaporation of the solvent and purification of the reaction product by methods previously described.

The compounds of Formula I, where L, R and A are as previously defined, can be prepared, as shown in Equation 5, by reaction of a sulfonyl carbamate of Formula VII and an amine of Formula III, by the methods described in South African Patent Application No. 825,042.

Equation 5

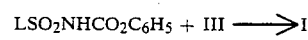

The compounds of Formula I where Q is S(O) and R and A are as previously defined can also be prepared by oxidation, by methods well known to those skilled in the art, of the compounds of Formula I where Q is S.

The sulfonamides of Formula IV can be prepared from the corresponding sulfonyl chlorides by methods well known in the art. When additional chemical reactions are required in the synthesis of sulfonamides of Formula IV, it is occasionally advantageous to convert the sulfonyl chlorides of Formula VII to a N-tert-butyl sulfonamide of Formula IX, followed by removal of the tert-butyl group; when all chemical modifications are complete, as shown in Equation 6.

Equation 6

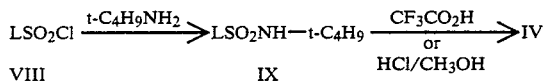

The preparation of sulfonamides of Formula IX are well known to those skilled in the art. The removal of the tert-butyl group can be carried out by (a) stirring a solution of the sulfonamide of Formula IX in trifluoroacetic acid for several hours, or (b) heating a solution of sulfonamides IX in methanol which contains hydrogen chloride or concentrated hydrochloric acid.

The sulfonyl chlorides of Formula VIII can be prepared by the methods shown in Equations 7A and 7B, both of which are well known in the art.

Equation 7

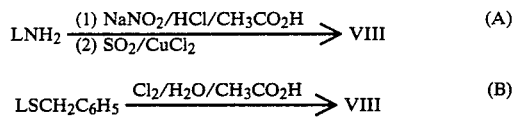

The amines of Formula III can be prepared by the methods described in (a) U.S. Pat. No. 4,339,267, (b) European Patent Application No. 46,677, (c) European Patent Application No. 73,562, (d) South African Patent Application No. 825,405 and (e) Vol. XIII and Vol. XVI of "The Chemistry of Heterocyclic Compounds," a series published by Interscience Publishers.

Agriculturally suitable salts of compounds of Formula I are also useful herbicides and can be prepared in a number of ways known to the art. For example, metal salts can be made by treating compounds of Formula I with a solution of alkali or alkaline earth metal salt having a sufficiently basic anion (e.g., hydroxide, alkoxide, carbonate or hydride). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The compounds of this invention are further illustrated by the following examples, wherein temperatures are given in degrees centigrade and parts are by weight unless otherwise indicated.

EXAMPLE 1

1,3-Dihydro-4-nitrobenzo[c]furan

A. A mixture of 100.0 g of methyl 2-methyl-3-nitrobenzoate, 100.0 g of N-bromosuccinimide, 3.0 g of dibenzoyl peroxide and 1000 ml of carbon tetrachloride was refluxed for 24 hours. The reaction mixture was cooled, 3.0 g of dibenzoyl peroxide added, and refluxing continued an additional 24 hours. The reaction mixture was cooled, filtered and the filtrate concentrated in vacuo. The crude reaction product was dissolved in ether and the organic solution washed sequentially with saturated sodium sulfite (500 ml), water (2×500 ml), 2.5% sodium hydroxide (500 ml), water (2×500 ml) and saturated brine (500 ml). The organic solution was dried over magnesium sulfate, filtered and the solvent evaporated in vacuo giving a pale yellow oily solid. Recrystallization from 350 ml of 1-chlorobutane/cyclohexane (2:1) gave 73.9 g of methyl 2-bromomethyl-3-nitrobenzoate, m.p. 67°–70°.

B. A solution of 54.8 g of methyl 2-bromomethyl-3-nitrobenzoate in a mixture of 200 ml dioxane and 45 ml water was refluxed for 72 hours. The reaction solution was cooled and concentrated in vacuo. The resulting solid was slurried in water, collected, washed with water and dried. Recrystallization from 1-chlorobutane gave 21.4 g of 1,3-dihydro-4-nitrobenzo[c]furan-1-one, m.p. 133.5°–136°.

C. A suspension of 19.5 g of 1,3-dihydro-4-nitrobenzo[c]furan-1-one in 100 ml of boron trifluoride etherate was cooled to 0°–5° under nitrogen. 125 ml of a 1M solution of borane-tetrahydrofuran complex was added dropwise below 10°. The orange suspension was allowed to warm to ambient temperature (H$_2$ evolution), and the reaction mixture exothermed to 30°. When the exotherm subsided (15–20 minutes), the mixture was refluxed 2.5 hours. The reaction mixture was cooled, decanted from some brown solids, and concentrated in vacuo to a yellow oil. The oil was cooled in an ice bath and acidified with dilute hydrochloric acid (H$_2$ evolution), then diluted with 300 ml water, and the suspension was extracted with ether. The organic solution was washed with brine, dried over magnesium sulfate, filtered, and the solvent evaporated in vacuo. The resulting yellow solid was purified by chromatography, eluting with methylene chloride to give 15.4 g of 1,3-dihydro-4-nitrobenzo[c]furan as a pale yellow solid, m.p. 104°–108°.

NMR (CDCl$_3$) δ: 5.15 (t, 2H, CH$_2$); 5.40 (t, 2H, CH$_2$); 7.3–7.7 (m, 2H, aromatic); and 8.0–8.3 (m, 1H, aromatic).

EXAMPLE 2

1,3-Dihydrobenzo[c]furan-4-amine

A solution of 66.8 g of tin (II) chloride dihydrate in 150 ml of concentrated hydrochloric acid was cooled to 10°–15° and 14.9 g of 1,3-dihydro-4-nitrobenzo[c]furan was added portionwise. The yellow suspension was allowed to warm to 25° at which temperature a slow exotherm occurred. The reaction mixture was maintained at 45° by cooling for 0.75 hour. The white suspension was cooled to 0°, the solid was collected, washed with cold concentrated hydrochloric acid and ethyl acetate giving 24.1 g of crude 1,3-dihydrobenzo[c]furan-4-amine hydrochloride, m.p. >250°.

A 2.0 g portion of the crude hydrochloride salt was dissolved in 50 ml water and the solution made strongly alkaline with 10% sodium hydroxide. The aqueous mixture was extracted with ether. The organic solution was washed with brine, dried over magnesium sulfate, and filtered. The solvent was evaporated in vacuo to give 0.5 g of 1,3-dihydrobenzo[c]furan-4-amine, m.p. 85°–89°.

IR(nujol mull): NH$_2$ (3365 and 3400 cm$^{-1}$).

NMR (CDCl$_3$) δ: 3.5 (broad s, 2H, NH$_2$); 5.0 (m, 4H, CH$_2$); and 6.5–7.3 (m, 3H, aromatic).

EXAMPLE 3

1,3-Dihydrobenzo[c]furan-4-sulfonamide

A. A suspension of 22.1 g of the crude hydrochloride salt prepared in Example 2 in a mixture of 30 ml of concentrated hydrochloric acid and 30 ml acetic acid was cooled to 0°–5°. A solution of 6.2 g of sodium nitrite in 15 ml water was added dropwise at 0°–5°. The thick suspension was diluted with 19 ml of concentrated hydrochloric acid to facilitate stirring and 1.0 g of sodium nitrite was added; stirring was continued for 1 hour. The suspension of the diazonium salt was added portionwise at 0°–5° to a stirred mixture of 80 ml of acetic acid, 25 ml of sulfur dioxide and 1.6 g of copper (II) chloride dihydrate. The resulting pale green suspension was allowed to warm to ambient temperature and stirred for 4.5 hours. The yellow-green solution was poured into 1000 ml of cold water and the aqueous mixture extracted three times with 1-chlorobutane. The combined organic solution was washed three times with water and saturated sodium bicarbonate solution, then dried over magnesium sulfate, and filtered. Evaporation of the solvent in vacuo gave 9.8 g of 1,3-dihydrobenzo[c]furan-4-sulfonyl chloride as a yellow oil which crystallized on cooling and scratching, m.p. 40°–43°.

NMR (CDCl$_3$) δ: 5.15 (t, 2H, CH$_2$); 5.40 (t, 2H, CH$_2$); and 7.15–8.10 (m, 3H, aromatic).

B. A solution of 9.8 g of the sulfonyl chloride, prepared in Part A, in 150 ml tetrahydrofuran was cooled to approximately 5°, and 6.6 ml of concentrated ammonium hydroxide was added dropwise. The resulting yellow suspension was allowed to warm to ambient temperature and stirred 0.5 hour; thin-layer chromatography showed the reaction was complete. The solvent was evaporated in vacuo and the resulting solid was slurried in 150 ml water, collected, washed with water and dried. The crude product was washed with 1-chlorobutane and dried to give 7.74 g of 1,3-dihydrobenzo[c]furan-4-sulfonamide, m.p. 153°–158°.

IR(nujol mull): SO$_2$NH$_2$ (3260 and 3380 cm$^{-1}$).

NMR (CDCl$_3$/DMSO-d$_6$)δ: 5.00 (t, 2H, CH$_2$); 5.23 (t, 2H, CH$_2$); 7.07 (broad s, 2H, NH$_2$); and 7.30–7.93 (m, 3H, aromatic).

EXAMPLE 4

1,3-Dihydrobenzo[c]furan-4-sulfonyl isocyanate

A mixture of 7.0 g of 1,3-dihydrobenzo[c]furan-4-sulfonamide, 4.0 ml of butyl isocyanate, 0.1 g of DABCO ® and 150 ml xylene was heated to reflux. Phosgene (3.1 ml) was added in small portions to the reaction mixture while maintaining the reaction temperature >130°. When addition of phosgene was complete, the reaction mixture was heated to reflux (128°) for 1 hour, then cooled under nitrogen. The reaction mixture was filtered under nitrogen, and the filtrate was concentrated in vacuo to give 1,3-dihydrobenzo[c]furan-4-sulfonyl isocyanate as an amber oil. The crude sulfonyl isocyanate was dissolved in methylene chloride (total volume=28 ml) for reaction with amino heterocycles.

IR(neat): SO$_2$NCO (2215 cm$^{-1}$).

EXAMPLE 5

1,3-Dihydro-N-[(4-methoxy-6-methylpyrimidin-2-yl)aminocarbonyl]benzo[c]furan-4-sulfonamide A 7.0 ml portion of the methylene chloride solution of 1,3-dihydrobenzo[c]furan-4-sulfonyl isocyanate prepared in Example 4 was added to a stirred suspension of 0.78 g of 4-methoxy-6-methylpyrimidin-2-amine in 20 ml of methylene chloride. After several minutes the amine dissolved, followed by formation of a precipitate. After stirring for 1.75 hours, the solid was collected, washed with methylene chloride and 1-chlorobutane, then dried to give 1.4 g of 1,3-dihydro-N-[(4-methoxy-6-methylpyrimidin-2-yl)aminocarbonyl]benzo[c]furan-4-sulfonamide, m.p. 190°–194° (d).

IR(nujol null): C=O (1725 cm$^{-1}$).

NMR (CDCl$_3$/TFA)δ: 2.6 (s, 3H, CH$_3$); 4.1 (s, 3H, OCH$_3$); 5.15 (broad s, 2H, CH$_2$); 5.45 (broad s, 2H, CH$_2$); 6.6 (s, 1H, pyrimidine CH); 7.5–7.8 (m, 2H, aromatic); and 7.8–8.2 (m, 1H, aromatic).

EXAMPLE 6

4-Nitrobenzo[c]thiophene-1(3H)-one

A. To a solution of 34.7 g of sodium methoxide in 600 ml methanol was added 57.9 g of 1,1-dimethylethanethiol below 25°. The resulting solution was stirred one hour before the portionwise addition of 172.7 g of methyl 2-bromomethyl-3-nitrobenzoate. The resulting suspension was refluxed two hours. The mixture was cooled, and the solvent evaporated in vacuo. The residual oil was partitioned between ether and water. The organic solution was washed twice with 2.5% sodium hydroxide solution, twice with water, followed by brine, then dried over magnesium sulfate, filtered and the filtrate concentrated in vacuo to give 164.2 g of crude methyl 2-[(1,1-dimethylethylthio)methyl]-3-nitrobenzoate as an oil.

B. A mixture of 149.2 g of the crude oil prepared in Part A, 40 g of p-toluenesulfonic acid and 500 ml of xylene was refluxed for 50 minutes. The dark brown soluution was cooled and the solvent evaporated in vacuo. Trituration of the resulting oil with ethanol gave a solid which was collected, washed twice with ethanol followed by hexane, then dried to give 65.4 g of 4-nitrobenzo[c]thiophene-1(3H)-one, m.p. 128°–133°.

IR(nujol mull): C=O (1660 cm$^{-1}$).

NMR (CDCl$_3$)δ: 4.85 (s, 2H, CH$_2$); and 7.52–8.65 (m, 3H, aromatic).

EXAMPLE 7

1,3-Dihydro-N-(1,1-dimethylethyl)-1-oxobenzo[c]thiophene-4-sulfonamide

A. 4-Nitrobenzo[c]thiophene-1(3H)-one (38.1 g) was added portionwise to a solution of 146.0 g of stannous chloride dihydrate in 325 ml concentrated hydrochloric acid. A slow exotherm from 18° to 42° occurred and the reaction mixture was maintained at 40°–45° by cooling. When the exotherm subsided, the suspension was stirred while cooling to ambient temperature (3.5 hours). The solid was collected, washed with a small volume of cold concentrated hydrochloric acid, then dried under nitrogen to give 57.7 g of crude 1,3-dihydro-1-oxobenzo[c]thiophene-4-amine hydrochloride, m.p. 205° (d).

B. A suspension of 57.7 g of the crude amine hydrochloride (prepared in Part A) in a mixture of 130 ml concentrated hydrochloric acid and 80 ml of acetic acid was cooled to 0°–5°. A solution of 14.9 g of sodium nitrite in 40 ml of H$_2$O was added dropwise at 0°–5°. The thick yellow suspension was stirred approximately 0.25 hour, then added portionwise to a stirred mixture of 65 ml of sulfur dioxide, 4.2 g of cupric chloride dihydrate, and 210 ml of acetic acid while keeping the reaction temperature at 5°–10°. The yellow-green suspension was allowed to warm to ambient temperature and stirred 2.5 hours. The reaction suspension was poured into 5000 ml H$_2$O; the solid was collected and washed twice with water. The crude product was dissolved in methylene chloride; the organic solution was dried over magnesium sulfate, filtered and concentrated in vacuo. The product was slurried in hexane, collected and dried to give 34.3 g of 1,3-dihydro-1-oxobenzo[c]thiophene sulfonyl chloride, m.p. 137°–140° (d).

IR(nujol mull): C=O (1680 cm$^{-1}$).

NMR (CDCl$_3$/TFA)δ: 5.0 (s, 2H, CH$_2$); 7.65–8.10 (m, 1H, aromatic); and 8.17–8.35 (m, 2H, aromatic).

C. A solution of 34.3 g of the sulfonyl chloride (prepared in Part B) in 500 ml tetrahydrofuran was cooled to 20° and 21.2 g of 1,1-dimethylethylamine was added dropwise below 25°. The yellow suspension was stirred at ambient temperature until thin-layer chromatography showed the reaction was complete. The amine hydrochloride was removed by filtration and washed with tetrahydrofuran. The combined filtrates were concentrated in vacuo to a yellow-brown oil which partially crystallized. The crude reaction product was partitioned between water and ether. The organic phase was washed with water and brine, then stirred with magnesium sulfate and charcoal and filtered through Celite ®. Concentration in vacuo of the filtrate gave an oil which crystallized on trituration with hexane. Recrystallization from cyclohexane/1-chlorobutane gave 31.5 g of 1,3-dihydro-N-(1,1-dimethylethyl)-1-oxobenzo[c]thiophene-4-sulfonamide, m.p. 121°–124°.

IR(nujol mull): NH (3295 cm$^{-1}$), C=O (1700 cm$^{-1}$).

NMR (CDCl$_3$)δ: 1.25 (s, 9H, t-Bu); 4.80 (s, 2H, CH$_2$); 5.48 (2, 1H, NH); and 7.57–8.40 (m, 3H, aromatic).

EXAMPLE 8

1,3-Dihydro-N-(1,1-dimethylethyl)benzo[c]thiophene-4-sulfonamide

A suspension of 8.0 g of 1,3-dihydro-N-(1,1-dimethylethyl)-1-oxobenzo[c]thiophene-4-sulfonamide in a mixture of 15 ml of tetrahydrofuran, 25 ml of boron trifluoride etherate was cooled to 10° under N$_2$, and 56 ml of a 1M solution of borane tetrahydrofuran complex was added dropwise at approximately 10°. The reaction mixture was allowed to warm to ambient temperature as a gas was evolved. When ambient temperature was reached, a slow exotherm to 31° occurred. When the exotherm subsided, the reaction mixture was heated to reflux for two hours, then cooled and allowed to stand overnight. The supernatant was decanted fom some brown solid, and concentrated in vacuo. The resulting yellow oil was cooled to approximately 5°, acidified with 5% hydrochloric acid (gas evolution), and diluted with 150 ml water. The aqueous mixture was extracted with ethyl acetate. The organic solution was washed twice with water, dried over magnesium sulfate, then filtered and the filtrate concentrated in vacuo. The resulting yellow oil was purified by chromatography, using methylene chloride as eluent, to give 3.6 g of 1,3-dihydro-N-(1,1-dimethylethyl)benzo[c]thiophene-4-sulfonamide, m.p. 128.5°–132°.

IR(nujol mull): NH (3310 cm$^{-1}$).

NMR (CDCl$_3$)δ: 1.2 (s, 9H, t-Bu); 4.23 (m, 2H, CH$_2$); 4.52 (m, 2H, CH$_2$); 5.22 (s, 1H, NH); 7.28–7.6 (m, 2H, aromatic); and 7.75–8.08 (m, 1H, aromatic).

EXAMPLE 9

1,3-Dihydrobenzo[c]thiophene-4-sulfonamide

A solution of 3.0 g of 1,3-dihydro-N-(1,1-dimethylethyl)benzo[c]thiophene-4-sulfonamide in 50 ml of trifluoroacetic acid was stirred at ambient temperature for 4 hours. The brown solution was concentrated in vacuo. 1-Chlorobutane was added to the resulting brown oil and the mixture concentrated in vacuo. Repeating this procedure gave an oil which on trituration with 1-chlorobutane gave a brown solid. Purification of the crude reaction product by chromatography, using hexane/ethyl acetate (3:2) as eluent gave 1.4 g of 1,3-dihydrobenzo[c]thiophene-4-sulfonamide as a pale yellow solid, m.p. 146°–148°.

IR(nujol mull): NH$_2$ (3270 and 3370 cm$^{-1}$).

NMR (CDCl$_3$/DMSO-d$_6$)δ: 4.19 (m, 2H, CH$_2$); 4.5 (m, 2H, CH$_2$); 6.8 (broad s, 2H, NH$_2$); and 7.2–8.0 (m, 3H, aromatic).

EXAMPLE 10

1,3-Dihydrobenzo[c]thiophene-4-sulfonyl isocyanate

A mixture of 5.5 g of 1,3-dihydrobenzo[c]thiophene-4-sulfonamide, 2.5 g of butyl isocyanate and 0.05 g of DABCO ® in 50 ml of xylene was heated to 135° and 2.2 ml of liquid phosgene was added in small portions at approximately 135°. When the addition of phosgene was complete, heating was continued for 5 minutes before the dark brown suspension was cooled to ambient temperature under a slow stream of nitrogen. The reaction mixture was filtered under nitrogen and the filtrate was concentrated in vacuo to give 1,3-dihydrobenzo[c]thiophene-4-sulfonyl isocyanate as a dark red-brown oil. The crude sulfonyl isocyanate was dissolved in methylene chloride (total volume=26 ml) for reaction with aminoheterocycles.

IR(neat): $SO_2NCO$ (2200 $cm^{-1}$).

EXAMPLE 11

1,3-Dihydro-N-[(4,6-dimethoxy-1,3,5-triazin-2-yl)aminocarbonyl]benzo[c]thiophene-4-sulfonamide A 4.5 ml portion of the methylene chloride solution prepared in Example 10 was added to a stirred suspension of 0.41 g of 4,6-dimethoxy-1,3,5-triazin-2-amine in 5 ml of methylene chloride, and the suspension stirred 2.5 days. The light purple solid was collected, washed with 1-chlorobutane and dried giving 0.91 g of 1,3-dihydro-N-[(4,6-dimethoxy-1,3,5-triazin-2-yl)]benzo[c]thiophene-4-sulfonamide, m.p. 190°–194° (d).

IR(nujol mull): C=O (1728 $cm^{-1}$).

NMR (CDCl$_3$/DMSO-d$_6$)δ: 4.0 (s, 6H, OCH$_3$); 4.25 (broad s, 2H, CH$_2$); 4.55 (broad s, 2H, CH$_2$); 7.1–8.2 (m, 4H, aromatic and NH); and 11.85 (broad s, 1H, NH).

EXAMPLE 12

1,3-Dihydro-N-(1,1-dimethylethyl)benzo[c]thiophene-4-sulfonamide 2,2-dioxide

A solution of 6.8 g of 1,3-dihydro-N-(1,1-dimethylethyl)benzo[c]thiophene-4-sulfonamide in 100 ml of acetic acid was warmed to 75°–80°, and 5.4 ml of 30% hydrogen peroxide was added dropwise. The reaction mixture was heated at 75°–80° for 1 hour, 2.0 ml of 30% hydrogen peroxide added, and heating continued for 1 hour at approximately 90°. The reaction solution was cooled to ambient temperature, and the suspension poured into 600 ml water. The solid was collected, washed with water and dried giving 5.9 g of 1,3-dihydro-N-(1,1-dimethylethyl)benzo[c]thiophene-4-sulfonamide 2,2-dioxide, m.p. 170° (s), 178° (d).

IR(nujol mull): NH (3255 $cm^{-1}$).

NMR (CDCl$_3$/DMSO-d$_6$)δ: 1.18 (s, 9H, t-C$_4$H$_9$); 4.40 (s, 2H, CH$_2$); 4.73 (s, 2H, CH$_2$); 7.35 (s, 1H, NH); 7.47–7.70 (m, 2H, aromatic); and 7.85–8.13 (m, 1H, aromatic).

EXAMPLE 13

1,3-Dihydrobenzo[c]thiophene-4-sulfonamide 2,2-dioxide

A solution of 5.9 g of the compound, prepared in Example 12, in 65 ml of trifluoroacetic acid was stirred at ambient temperature for 1.25 hours. The solvent was evaporated; 1-chlorobutane was added to the residual oil, and the mixture was concentrated. This process was repeated with ethyl acetate. The crude reaction product was triturated with a warm mixture of 1-chlorobutane and ethyl acetate. The solid was collected, washed with 1-chlorobutane and dried to give 4.6 g of 1,3-dihydrobenzo[c]thiophene-4-sulfonamide 2,2-dioxide, m.p. 174.5°–178° (d).

IR(nujol mull): $SO_2NH_2$ (3270 and 3370 $cm^{-1}$).

NMR (CDCl$_3$/DMSO-d$_6$)δ: 4.40 (s, 2H, CH$_2$); 4.75 (s, 2H, CH$_2$); 7.3 (s, 2H, NH$_2$); and 7.5–8.15 (m, 3H, aromatic).

EXAMPLE 14

1,3-Dihydro-N-[(4,6-dimethoxypyrimidin-2-yl)aminocarbonyl]benzo[c]thiophene-4-sulfonamide 2,2-dioxide A suspension of 0.74 g of the sulfonamide prepared in Example 13 in 50 ml of methylene chloride was cooled to 10° to 15° under nitrogen, and 1.17 ml of a 2M solution of trimethylaluminum in toluene was added slowly. The suspension was allowed to warm to room temperature, 0.67 g of methyl N-(4,6-dimethoxypyrimidin-2-yl)carbamate was added, and the reaction mixture was heated at reflux overnight. The turbid solution was cooled to 0°–5° and 50 ml of 5% hydrochloric acid was added dropwise. The two-phase suspension was allowed to warm to ambient temperature, then filtered. The solid was washed with 1-chlorobutane and dried giving 0.31 g of 1,3-dihydro-N-[(4,6-dimethoxypyrimidin-2-yl)aminocarbonyl]benzo[c]thiophene-4-sulfonamide, 2,2-dioxide, m.p. 170°–173° (d).

IR(nujol mull): C=O (1730 $cm^{-1}$).

NMR (CDCl$_3$)δ: 3.95 (s, 6H, OCH$_3$); 4.39 (s, 2H, CH$_2$); 4.89 (s, 2H, CH$_2$); 5.8 (s, 1H, pyrimidine CH); 7.6 (m, 2H, aromatic); and 8.15 (m, 1H, aromatic).

EXAMPLE 15

N-(1,1-Dimethylethyl)-2-methyl-2,3-dihydro-1,3-dioxo-1H-isoindole-4-sulfonamide

A. Phenylmethanethiol (43.4 g) was added to a solution of 22.9 g of 85.6% potassium hydroxide in 300 ml of methanol. The solution was stirred approximately 15 minutes and concentrated in vacuo. The salt was dissolved in 200 ml of dimethylformamide and added dropwise to a solution of 72.1 g of 2-methyl-4-nitroisoindole-1,3-(2H)-dione in 200 ml dimethylformamide, keeping the reaction temperature approximately 25° by cooling. The reaction mixture was stirred 2.25 hours at ambient temperature and then poured into 4000 ml cold water. The pale yellow solid was collected, washed twice with water followed by ethanol and dried to give 94.1 g of 2-methyl-4-(phenylmethylthio)-1H-isoindole-1,3-(2H)-dione, m.p. 180°–187°.

B. A suspension of 78.5 g of the compound prepared in Part A in 750 ml acetic acid and 50 ml water was cooled to 5°–10° and 44.3 ml of liquid chlorine was added dropwise below 15°. The suspension was stirred 0.5 hour at approximately 10°, then poured into 2000 ml water. The solid was collected, washed twice with water followed by a mixture of hexane/1-chlorobutane (1:1) and dried to give 66.9 g of 1,3-dioxo-2,3-dihydro-2- methyl-1H-isoindole-4-sulfonyl chloride, m.p. 159°–162.5°.

IR(nujol mull): C=O (1715 and 1770 cm$^{-1}$).

NMR (CDCl$_3$)δ: 3.27 (s, 3H, NCH$_3$); and 7.75–8.50 (m, 3H, aromatic).

C. 16.1 g of 1,1-Dimethylethylamine in 50 ml of tetrahydrofuran was added dropwise to a solution of 25.9 g of the sulfonyl chloride prepared in Part B in 300 ml of tetrahydrofuran. The addition caused the reaction temperature to rise to 40°. The suspension was stirred 3 hours at ambient temperature, then filtered, and the filtrate concentrated in vacuo. Recrystallization of the crude product from 1-chlorobutane gave 19.2 g of N-(1,1-dimethylethyl)-2,3-dihydro-1,3-dioxo-2-methyl-1H-isoindole-4-sulfonamide, m.p. 160°–163°.

IR(nujol mull): NH (3260 cm$^{-1}$)

NMR (CDCl$_3$)δ: 1.27 (s, 9H, t-C$_4$H$_9$); 3.13 (s, 3H, NCH$_3$); 6.55 (broad s, 1H, NH); and 7.70–8.37 (m, 3H, aromatic).

EXAMPLE 16

2,3-Dihydro-N-(1,1-dimethylethyl)-2-methyl-1H-isoindole-4-sulfonamide-borane complex A solution of 14.8 g of the compound prepared in Example 15 in 200 ml tetrahydrofuran was cooled to 5°–10° under nitrogen, and 200 ml of a 1M solution of borane-tetrahydrofuran complex was added dropwise. The reaction solution was allowed to warm to ambient temperature, and then heated slowly to reflux (gas evolution). The reaction mixture was refluxed overnight during which time a light yellow suspension formed. The reaction mixture was cooled to below 15°, 75 ml of water was added cautiously (gas evolution), and the reaction mixture was concentrated in vacuo. The oily solid was partitioned between water and ether. The organic phase was washed with water and brine, dried over magnesium sulfate, filtered and the solvent evaporated in vacuo. The crude reaction product was slurried in 1-chlorobutane. The solid was collected, washed with 1-chlorobutane and dried to give 8.5 g of 2,3-dihydro-N-(1,1-dimethylethyl)-2-methyl-1H-isoindole-4-sulfonamide-borane complex; m.p. 140°–143° (d).

IR(nujol mull): NH (3320 cm$^{-1}$), BH$_3$ (2280, 2330, 2370 cm$^{-1}$).

NMR (CDCl$_3$)δ: 1.23 (s, 9H, t-C$_4$H$_9$); 2.84 (s, 3H, NCH$_3$); 4.0–5.05 (m, 5H, CH$_2$ and NH); and 7.45–8.0 (m, 3H, aromatic).

EXAMPLE 17

2,3-Dihydro-2-methyl-1H-isoindole-4-sulfonamide hydrochloride

A suspension of 5.3 g of the compound prepared in Example 16 in 20 ml of methanol was cooled to 10° and 50 ml of concentrated hydrochloric acid was added dropwise at 10°–15° (gas evolution). The reaction mixture was allowed to warm to room temperature and then refluxed 3.75 hours. The reaction solution was cooled and concentrated in vacuo. The white solid was washed with ethanol followed by ethyl acetate then dried to give 4.1 g of 2,3-dihydro-2-methyl-1H-isoindole-4-sulfonamide hydrochloride, m.p. >250°.

IR(nujol mull): NH$_2$ (3150 and 3220 cm$^{-1}$).

NMR (DMSO-d$_6$): 3.0 (s, 3H, NCH$_3$); 4.63 (broad s, 2H, CH$_2$); 4.8 (broad s, 2H, CH$_2$); 7.6–8.2 (m, 5H, aromatic and NH$_2$); and 13.6 (broad s, 1H, N⊕-H).

TABLE I

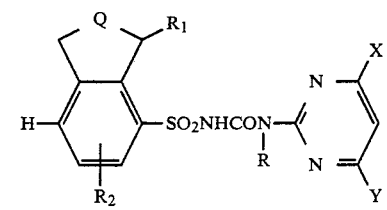

| Q | R$_1$ | R$_2$ | R | X | Y | m.p. (°C.) |
|---|---|---|---|---|---|---|
| O | H | H | H | CH$_3$ | OCH$_3$ | 190–194° (d) |
| O | H | H | H | OCH$_3$ | OCH$_3$ | 225–229° (d) |
| O | H | H | H | CH$_3$ | CH$_3$ | |
| O | H | H | H | C$_2$H$_5$ | OCH$_3$ | |
| O | H | H | H | OC$_2$H$_5$ | CH$_3$ | |
| O | H | H | H | OC$_2$H$_5$ | OCH$_3$ | |
| O | H | H | H | Cl | OCH$_3$ | |
| O | H | H | H | Br | OCH$_3$ | |
| O | H | H | H | F | OCH$_3$ | |
| O | H | H | H | OCF$_2$H | CH$_3$ | |
| O | H | H | H | OCF$_2$H | OCH$_3$ | |
| O | H | H | H | OCF$_2$H | OCF$_2$H | |
| O | H | H | H | OCF$_2$H | CF$_3$ | |
| O | H | H | H | CF$_3$ | CF$_3$ | |
| O | H | H | H | CF$_3$ | OCH$_3$ | |
| O | H | H | H | CF$_3$ | OC$_2$H$_5$ | |
| O | H | H | H | OCH$_3$ | H | |
| O | H | H | H | OCH$_3$ | NH$_2$ | |
| O | H | H | H | OCH$_3$ | NHCH$_3$ | |
| O | H | H | H | OCH$_3$ | N(CH$_3$)$_2$ | |
| O | H | H | H | OCH$_3$ | n-C$_4$H$_9$ | |
| O | H | H | H | OCH$_3$ | CH$_2$OCH$_3$ | |
| O | H | H | H | OCH$_3$ | CH$_2$OC$_2$H$_5$ | |
| O | H | H | H | CH$_3$ | O—i-C$_3$H$_7$ | |
| O | H | H | H | CH$_3$ | O—n-C$_4$H$_9$ | |

TABLE I-continued

Structure:

$$\text{H-Ar(Q-CH}_2\text{, R}_1\text{, R}_2\text{)-SO}_2\text{NHCON(R)-pyrimidine(X,Y)}$$

| Q | R₁ | R₂ | R | X | Y | m.p. (°C.) |
|---|---|---|---|---|---|---|
| O | H | H | H | CH₃ | OCH₂CH=CH₂ | |
| O | H | H | H | CH₃ | OCH₂C≡CH | |
| O | H | H | H | CH₃ | OCH₂CH₂OCH₃ | |
| O | H | H | H | CH₃ | OCH₂CH₂F | |
| O | H | H | H | CH₃ | OCH₂CH₂Cl | |
| O | H | H | H | CH₃ | OCH₂CH₂Br | |
| O | H | H | H | CH₃ | CH(OCH₃)₂ | |
| O | H | H | H | CH₃ | CH(OC₂H₅)₂ | |
| O | H | H | H | CH₃ | OCH₂C(CH₃)=CH₂ | |
| O | H | H | H | CH₃ | OCH₂C≡CCH₃ | |
| O | H | H | H | OCH₃ | SCH₃ | |
| O | H | H | H | OCH₃ | SC₂H₅ | |
| O | H | H | H | OCH₃ | CH(OCH₃)₂ | |
| O | H | H | H | OCH₃ | CH(OC₂H₅)₂ | |
| O | H | H | H | OCH₃ | (1,3-dioxolan-2-yl) | |
| O | H | H | H | OCH₃ | (1,3-dioxan-2-yl) | |
| O | H | H | H | OCH₃ | CH₂Cl | |
| O | H | H | H | OCH₃ | SCF₂H | |
| O | H | H | H | CH₃ | OCF₂CF₂H | |
| O | H | H | H | CH₃ | OCF₂CHCF | |
| O | H | H | H | CH₃ | OCF₂CHBrF | |
| O | H | H | H | CH₃ | OCF₂CHFCF₃ | |
| O | H | H | H | CH₃ | OCH₂CF₃ | |
| O | CH₃ | H | H | OCH₃ | OCH₃ | |
| O | H | Cl | H | CH₃ | OCH₃ | |
| O | H | Br | H | CH₃ | OCH₃ | |
| O | H | OCH₃ | H | OCH₃ | OCH₃ | |
| O | H | OC₂H₅ | H | OCH₃ | OCH₃ | |
| O | H | O—n-C₃H₇ | H | OCH₃ | OCH₃ | |
| O | H | CF₃ | H | OCH₃ | OCH₃ | |
| O | H | H | CH₃ | OCH₃ | OCH₃ | |
| S | H | H | H | CH₃ | OCH₃ | 203–206° (d) |
| S | H | H | H | CH₃ | CH₃ | |
| S | H | H | H | OCH₃ | OCH₃ | 210–213° (d) |
| S | H | H | H | Cl | OCH₃ | 203–206° (d) |
| S | H | H | H | Br | OCH₃ | |
| S | H | H | H | F | OCH₃ | |
| S | H | H | H | OCF₂H | OCH₃ | |
| S | H | H | H | CF₃ | OCH₃ | |
| S | H | H | H | OC₂H₅ | OCH₃ | |
| S | H | H | H | C₂H₅ | OCH₃ | |
| S | H | H | H | OCF₂H | OCF₂H | 202.5–205° |
| S | H | H | H | CH₃ | OCF₂H | |
| S | H | H | H | OCH₃ | CH(OCH₃)₂ | |
| S | H | H | H | OCH₃ | SCH₃ | |
| S(O) | H | H | H | CH₃ | OCH₃ | |
| S(O) | H | H | H | CH₃ | CH₃ | |
| S(O) | H | H | H | OCH₃ | OCH₃ | |
| S(O) | H | H | H | Cl | OCH₃ | |
| S(O) | H | H | H | Br | OCH₃ | |
| S(O) | H | H | H | F | OCH₃ | |
| S(O) | H | H | H | OCF₂H | OCH₃ | |
| S(O) | H | H | H | CF₃ | OCH₃ | |
| S(O) | H | H | H | OC₂H₅ | OCH₃ | |
| S(O) | H | H | H | C₂H₅ | OCH₃ | |
| S(O) | H | H | H | OCF₂H | OCF₂H | |
| S(O) | H | H | H | CH₃ | OCF₂H | |
| S(O) | H | H | H | OCH₃ | CH(OCH₃)₂ | |
| SO₂ | H | H | H | CH₃ | OCH₃ | |

TABLE I-continued

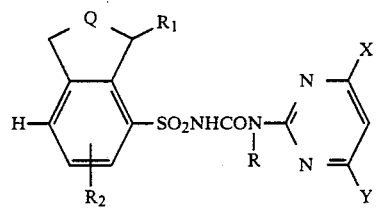

| Q | R₁ | R₂ | R | X | Y | m.p. (°C.) |
|---|---|---|---|---|---|---|
| SO₂ | H | H | H | CH₃ | CH₃ | |
| SO₂ | H | H | H | OCH₃ | OCH₃ | 170–173° (d) |
| SO₂ | H | H | H | Cl | OCH₃ | |
| SO₂ | H | H | H | Br | OCH₃ | |
| SO₂ | H | H | H | F | OCH₃ | |
| SO₂ | H | H | H | OCF₂H | OCH₃ | |
| SO₂ | H | H | H | CF₃ | OCH₃ | |
| SO₂ | H | H | H | OC₂H₅ | OCH₃ | |
| SO₂ | H | H | H | C₂H₅ | OCH₃ | |
| SO₂ | H | H | H | OCF₂H | OCF₂H | |
| SO₂ | H | H | H | CH₃ | OCF₂H | |
| SO₂ | H | H | H | OCH₃ | CH(OCH₃)₂ | |
| SO₂ | H | H | H | OCH₃ | SCH₃ | |
| NH | H | H | H | CH₃ | OCH₃ | |
| NH | H | H | H | CH₃ | CH₃ | |
| NH | H | H | H | OCH₃ | OCH₃ | |
| NCH₃ | H | H | H | CH₃ | OCH₃ | |
| NCH₃ | H | H | H | CH₃ | CH₃ | |
| NCH₃ | H | H | H | OCH₃ | OCH₃ | |
| NC₂H₅ | H | H | H | CH₃ | OCH₃ | |
| NC₂H₅ | H | H | H | CH₃ | CH₃ | |
| NC₂H₅ | H | H | H | OCH₃ | OCH₃ | |
| N—i-C₃H₇ | H | H | H | CH₃ | OCH₃ | |
| N—i-C₃H₇ | H | H | H | CH₃ | CH₃ | |
| N—i-C₃H₇ | H | H | H | OCH₃ | OCH₃ | |

TABLE Ia

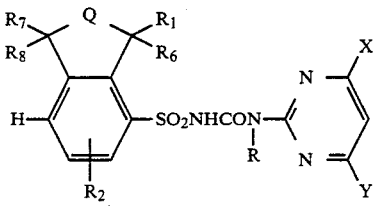

| Q | R₁ | R₂ | R₆ | R₇ | R₈ | R | X | Y | m.p. (°C.) |
|---|---|---|---|---|---|---|---|---|---|
| O | Cl | H | Cl | Cl | Cl | H | OCH₃ | OCH₃ | |
| O | F | H | F | F | F | H | OCH₃ | OCH₃ | |
| S | Cl | H | Cl | Cl | Cl | H | OCH₃ | OCH₃ | |

TABLE Ia-continued

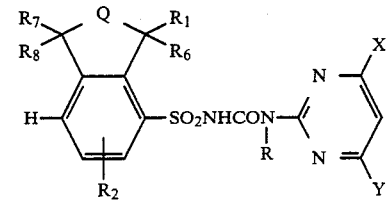

| Q | R₁ | R₂ | R₆ | R₇ | R₈ | R | X | Y | m.p. (°C.) |
|---|---|---|---|---|---|---|---|---|---|
| S | F | H | F | F | F | H | OCH₃ | OCH₃ | |

TABLE II

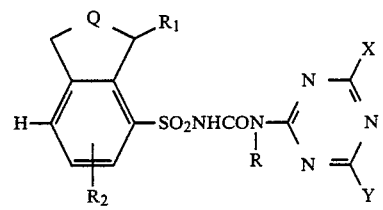

| Q | R₁ | R₂ | R | X | Y | m.p. (°C.) |
|---|---|---|---|---|---|---|
| O | H | H | H | CH₃ | OCH₃ | 199–202° (d) |
| O | H | H | H | OCH₃ | OCH₃ | 202–205° (d) |
| O | H | H | H | CH₃ | CH₃ | |
| O | H | H | H | C₂H₅ | OCH₃ | |
| O | H | H | H | OC₂H₅ | CH₃ | |
| O | H | H | H | OC₂H₅ | OCH₃ | |
| O | H | H | H | OCF₂H | CH₃ | |
| O | H | H | H | OCF₂H | OCH₃ | |
| O | H | H | H | OCF₂H | OCF₂H | |
| O | H | H | H | OCF₂H | CF₃ | |
| O | H | H | H | CF₃ | CF₃ | |

TABLE II-continued

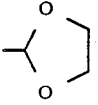

| Q | R₁ | R₂ | R | X | Y | m.p. (°C.) |
|---|----|----|---|---|---|------------|
| O | H | H | H | CF₃ | OCH₃ | |
| O | H | H | H | CF₃ | OC₂H₅ | |
| O | H | H | H | OCH₃ | H | |
| O | H | H | H | OCH₃ | NH₂ | |
| O | H | H | H | OCH₃ | NHCH₃ | |
| O | H | H | H | OCH₃ | N(CH₃)₂ | |
| O | H | H | H | OCH₃ | n-C₄H₉ | |
| O | H | H | H | OCH₃ | CH₂OCH₃ | |
| O | H | H | H | OCH₃ | CH₂OC₂H₅ | |
| O | H | H | H | CH₃ | O—i-C₃H₇ | |
| O | H | H | H | CH₃ | O—n-C₄H₉ | |
| O | H | H | H | CH₃ | OCH₂CH=CH₂ | |
| O | H | H | H | CH₃ | OCH₂C≡CH | |
| O | H | H | H | CH₃ | OCH₂CH₂OCH₃ | |
| O | H | H | H | CH₃ | OCH₂CH₂F | |
| O | H | H | H | CH₃ | OCH₂CH₂Cl | |
| O | H | H | H | CH₃ | OCH₂CH₂Br | |
| O | H | H | H | CH₃ | CH(OCH₃)₂ | |
| O | H | H | H | CH₃ | CH(OC₂H₅)₂ | |
| O | H | H | H | CH₃ | OCH₂C(CH₃)=CH₂ | |
| O | H | H | H | CH₃ | OCH₂C≡CCH₃ | |
| O | H | H | H | OCH₃ | SCH₃ | |
| O | H | H | H | OCH₃ | SC₂H₅ | |
| O | H | H | H | OCH₃ | CH(OCH₃)₂ | |
| O | H | H | H | OCH₃ | CH(OC₂H₅)₂ | |
| O | H | H | H | OCH₃ | 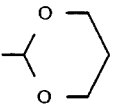 | |
| O | H | H | H | OCH₃ | | |
| O | H | H | H | OCH₃ | CH₂Cl | |
| O | H | H | H | OCH₃ | SCF₂H | |
| O | H | H | H | CH₃ | OCF₂CF₂H | |
| O | H | H | H | CH₃ | OCF₂CHCF | |
| O | H | H | H | CH₃ | OCF₂CHBrF | |
| O | H | H | H | CH₃ | OCF₂CHFCF₃ | |
| O | H | H | H | CH₃ | OCH₂CF₃ | |
| O | CH₃ | H | H | OCH₃ | OCH₃ | |
| O | H | Cl | H | CH₃ | OCH₃ | |
| O | H | Br | H | CH₃ | OCH₃ | |
| O | H | OCH₃ | H | OCH₃ | OCH₃ | |
| O | H | OC₂H₅ | H | OCH₃ | OCH₃ | |
| O | H | O—n-C₃H₇ | H | OCH₃ | OCH₃ | |
| O | H | CF₃ | H | OCH₃ | OCH₃ | |
| O | H | H | CH₃ | OCH₃ | OCH₃ | |
| S | H | H | H | CH₃ | OCH₃ | 180.5–185° (d) |
| S | H | H | H | CH₃ | CH₃ | |
| S | H | H | H | OCH₃ | OCH₃ | 190–194° (d) |
| S | H | H | H | OCF₂H | OCH₃ | |
| S | H | H | H | CF₃ | OCH₃ | |
| S | H | H | H | OC₂H₅ | OCH₃ | |
| S | H | H | H | C₂H₅ | OCH₃ | |
| S | H | H | H | OCF₂H | OCF₂H | |
| S | H | H | H | CH₃ | OCF₂H | |
| S | H | H | H | OCH₃ | CH(OCH₃)₂ | |
| S | H | H | H | OCH₃ | SCH₃ | |
| S(O) | H | H | H | CH₃ | OCH₃ | |
| S(O) | H | H | H | CH₃ | CH₃ | |
| S(O) | H | H | H | OCH₃ | OCH₃ | |
| S(O) | H | H | H | OCF₂H | OCH₃ | |
| S(O) | H | H | H | CF₃ | OCH₃ | |

TABLE II-continued

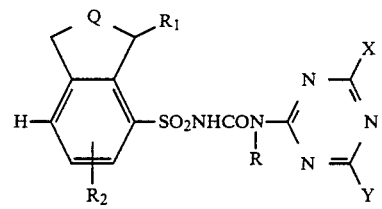

| Q | R₁ | R₂ | R | X | Y | m.p. (°C.) |
|---|---|---|---|---|---|---|
| S(O) | H | H | H | OC₂H₅ | OCH₃ | |
| S(O) | H | H | H | C₂H₅ | OCH₃ | |
| S(O) | H | H | H | OCF₂H | OCF₂H | |
| S(O) | H | H | H | CH₃ | OCF₂H | |
| S(O) | H | H | H | OCH₃ | CH(OCH₃)₂ | |
| SO₂ | H | H | H | CH₃ | OCH₃ | 183–186° (d) |
| SO₂ | H | H | H | CH₃ | CH₃ | |
| SO₂ | H | H | H | OCH₃ | OCH₃ | |
| SO₂ | H | H | H | OCF₂H | OCH₃ | |
| SO₂ | H | H | H | CF₃ | OCH₃ | |
| SO₂ | H | H | H | OC₂H₅ | OCH₃ | |
| SO₂ | H | H | H | C₂H₅ | OCH₃ | |
| SO₂ | H | H | H | OCF₂H | OCF₂H | |
| SO₂ | H | H | H | CH₃ | OCF₂H | |
| SO₂ | H | H | H | OCH₃ | CH(OCH₃)₂ | |
| SO₂ | H | H | H | OCH₃ | SCH₃ | |
| NH | H | H | H | CH₃ | OCH₃ | |
| NH | H | H | H | CH₃ | CH₃ | |
| NH | H | H | H | OCH₃ | OCH₃ | |
| NCH₃ | H | H | H | CH₃ | OCH₃ | |
| NCH₃ | H | H | H | CH₃ | CH₃ | |
| NCH₃ | H | H | H | OCH₃ | OCH₃ | |
| NC₂H₅ | H | H | H | CH₃ | OCH₃ | |
| NC₂H₅ | H | H | H | CH₃ | CH₃ | |
| NC₂H₅ | H | H | H | OCH₃ | OCH₃ | |
| N—i-C₃H₇ | H | H | H | CH₃ | OCH₃ | |
| N—i-C₃H₇ | H | H | H | CH₃ | CH₃ | |
| N—i-C₃H₇ | H | H | H | OCH₃ | OCH₃ | |

TABLE IIa

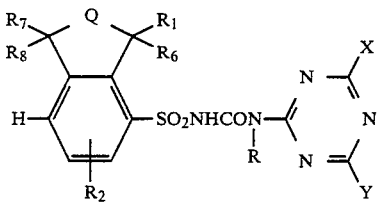

| Q | R₁ | R₂ | R₆ | R₇ | R₈ | R | X | Y | m.p. (°C.) |
|---|---|---|---|---|---|---|---|---|---|
| O | Cl | H | Cl | Cl | Cl | H | OCH₃ | OCH₃ | |
| O | F | H | F | F | F | H | OCH₃ | OCH₃ | |
| S | Cl | H | Cl | Cl | Cl | H | OCH₃ | OCH₃ | |

TABLE IIa-continued

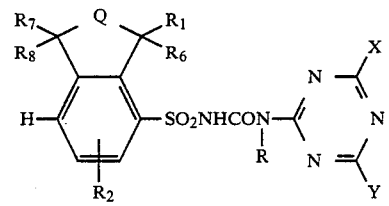

| Q | R₁ | R₂ | R₆ | R₇ | R₈ | R | X | Y | m.p. (°C.) |
|---|---|---|---|---|---|---|---|---|---|
| S | F | H | F | F | F | H | OCH₃ | OCH₃ | |

TABLE III

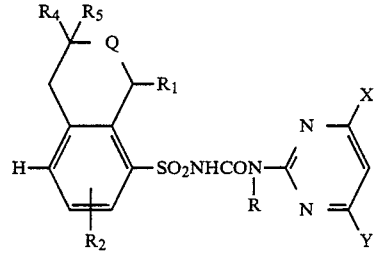

| Q | R₁ | R₂ | R₄ | R₅ | R | X | Y | m.p. (°C.) |
|---|---|---|---|---|---|---|---|---|
| O | H | H | H | H | H | CH₃ | OCH₃ | |
| O | H | H | H | H | H | OCH₃ | OCH₃ | |
| O | H | H | H | H | H | CH₃ | CH₃ | |
| O | H | H | H | H | H | C₂H₅ | OCH₃ | |
| O | H | H | H | H | H | OC₂H₅ | CH₃ | |
| O | H | H | H | H | H | OC₂H₅ | OCH₃ | |

TABLE III-continued

| Q | R₁ | R₂ | R₄ | R₅ | R | X | Y | m.p. (°C.) |
|---|---|---|---|---|---|---|---|---|
| O | H | H | H | H | H | Cl | OCH₃ | |
| O | H | H | H | H | H | Br | OCH₃ | |
| O | H | H | H | H | H | F | OCH₃ | |
| O | H | H | H | H | H | OCF₂H | CH₃ | |
| O | H | H | H | H | H | OCF₂H | OCH₃ | |
| O | H | H | H | H | H | OCF₂H | OCF₂H | |
| O | H | H | H | H | H | OCF₂H | CF₃ | |
| O | H | H | H | H | H | CF₃ | CF₃ | |
| O | H | H | H | H | H | CF₃ | OCH₃ | |
| O | H | H | H | H | H | CF₃ | OC₂H₅ | |
| O | H | H | H | H | H | OCH₃ | H | |
| O | H | H | H | H | H | OCH₃ | NH₂ | |
| O | H | H | H | H | H | OCH₃ | NHCH₃ | |
| O | H | H | H | H | H | OCH₃ | N(CH₃)₂ | |
| O | H | H | H | H | H | OCH₃ | n-C₄H₉ | |
| O | H | H | H | H | H | OCH₃ | CH₂OCH₃ | |
| O | H | H | H | H | H | OCH₃ | CH₂OC₂H₅ | |
| O | H | H | H | H | H | CH₃ | O—i-C₃H₇ | |
| O | H | H | H | H | H | CH₃ | O—n-C₄H₉ | |
| O | H | H | H | H | H | CH₃ | OCH₂CH=CH₂ | |
| O | H | H | H | H | H | CH₃ | OCH₂C≡CH | |
| O | H | H | H | H | H | CH₃ | OCH₂CH₂OCH₃ | |
| O | H | H | H | H | H | CH₃ | OCH₂CH₂F | |
| O | H | H | H | H | H | CH₃ | OCH₂CH₂Cl | |
| O | H | H | H | H | H | CH₃ | OCH₂CH₂Br | |
| O | H | H | H | H | H | CH₃ | CH(OCH₃)₂ | |
| O | H | H | H | H | H | CH₃ | CH(OC₂H₅)₂ | |
| O | H | H | H | H | H | CH₃ | OCH₂C(CH₃)=CH₂ | |
| O | H | H | H | H | H | CH₃ | OCH₂C≡CCH₃ | |
| O | H | H | H | H | H | OCH₃ | SCH₃ | |
| O | H | H | H | H | H | OCH₃ | SC₂H₅ | |
| O | H | H | H | H | H | OCH₃ | CH(OCH₃)₂ | |
| O | H | H | H | H | H | OCH₃ | CH(OC₂H₅)₂ | |
| O | H | H | H | H | H | OCH₃ | (1,3-dioxolan-2-yl) | |
| O | H | H | H | H | H | OCH₃ | (1,3-dioxan-2-yl) | |
| O | H | H | H | H | H | OCH₃ | CH₂Cl | |
| O | H | H | H | H | H | OCH₃ | SCF₂H | |
| O | H | H | H | H | H | CH₃ | OCF₂CF₂H | |
| O | H | H | H | H | H | CH₃ | OCF₂CHCF | |
| O | H | H | H | H | H | CH₃ | OCF₂CHBrF | |
| O | H | H | H | H | H | CH₃ | OCF₂CHFCF₃ | |
| O | H | H | H | H | H | CH₃ | OCH₂CF₃ | |
| O | CH₃ | H | H | H | H | OCH₃ | OCH₃ | |
| O | H | Cl | H | H | H | CH₃ | OCH₃ | |
| O | H | Br | H | H | H | CH₃ | OCH₃ | |
| O | H | OCH₃ | H | H | H | OCH₃ | OCH₃ | |
| O | H | OC₂H₅ | H | H | H | OCH₃ | OCH₃ | |
| O | H | O—n-C₃H₇ | H | H | H | OCH₃ | OCH₃ | |
| O | H | CF₃ | H | H | H | OCH₃ | OCH₃ | |
| O | H | H | H | H | CH₃ | OCH₃ | OCH₃ | |
| S | H | H | H | H | H | CH₃ | OCH₃ | |
| S | H | H | H | H | H | CH₃ | CH₃ | |
| S | H | H | H | H | H | OCH₃ | OCH₃ | |
| S | H | H | H | H | H | Cl | OCH₃ | |
| S | H | H | H | H | H | Br | OCH₃ | |
| S | H | H | H | H | H | F | OCH₃ | |
| S | H | H | H | H | H | OCF₂H | OCH₃ | |

TABLE III-continued

Structure: aromatic ring with substituents — CH(R₄)(R₅)-Q-CH(R₁)- forming a fused ring, SO₂NHCON(R)- linked to pyrimidine bearing X and Y, R₂ on ring.

| Q | R₁ | R₂ | R₄ | R₅ | R | X | Y | m.p. (°C.) |
|---|---|---|---|---|---|---|---|---|
| S | H | H | H | H | H | CF₃ | OCH₃ | |
| S | H | H | H | H | H | OC₂H₅ | OCH₃ | |
| S | H | H | H | H | H | C₂H₅ | OCH₃ | |
| S | H | H | H | H | H | OCF₂H | OCF₂H | |
| S | H | H | H | H | H | CH₃ | OCF₂H | |
| S | H | H | H | H | H | OCH₃ | CH(OCH₃)₂ | |
| S | H | H | H | H | H | OCH₃ | SCH₃ | |
| S(O) | H | H | H | H | H | CH₃ | OCH₃ | |
| S(O) | H | H | H | H | H | CH₃ | CH₃ | |
| S(O) | H | H | H | H | H | OCH₃ | OCH₃ | |
| S(O) | H | H | H | H | H | Cl | OCH₃ | |
| S(O) | H | H | H | H | H | Br | OCH₃ | |
| S(O) | H | H | H | H | H | OCF₂H | OCH₃ | |
| S(O) | H | H | H | H | H | CF₃ | OCH₃ | |
| S(O) | H | H | H | H | H | OC₂H₅ | OCH₃ | |
| S(O) | H | H | H | H | H | C₂H₅ | OCH₃ | |
| S(O) | H | H | H | H | H | OCF₂H | OCF₂H | |
| S(O) | H | H | H | H | H | CH₃ | OCF₂H | |
| S(O) | H | H | H | H | H | OCH₃ | CH(OCH₃)₂ | |
| S(O) | H | H | H | H | H | F | OCH₃ | |
| SO₂ | H | H | H | H | H | CH₃ | OCH₃ | |
| SO₂ | H | H | H | H | H | CH₃ | CH₃ | |
| SO₂ | H | H | H | H | H | OCH₃ | OCH₃ | |
| SO₂ | H | H | H | H | H | Cl | OCH₃ | |
| SO₂ | H | H | H | H | H | F | OCH₃ | |
| SO₂ | H | H | H | H | H | Br | OCH₃ | |
| SO₂ | H | H | H | H | H | OCF₂H | OCH₃ | |
| SO₂ | H | H | H | H | H | CF₃ | OCH₃ | |
| SO₂ | H | H | H | H | H | OC₂H₅ | OCH₃ | |
| SO₂ | H | H | H | H | H | C₂H₅ | OCH₃ | |
| SO₂ | H | H | H | H | H | OCF₂H | OCF₂H | |
| SO₂ | H | H | H | H | H | CH₃ | OCF₂H | |
| SO₂ | H | H | H | H | H | OCH₃ | CH(OCH₃)₂ | |
| SO₂ | H | H | H | H | H | OCH₃ | SCH₃ | |
| NH | H | H | H | H | H | CH₃ | OCH₃ | |
| NH | H | H | H | H | H | CH₃ | CH₃ | |
| NH | H | H | H | H | H | OCH₃ | OCH₃ | |
| NCH₃ | H | H | H | H | H | CH₃ | OCH₃ | |
| NCH₃ | H | H | H | H | H | CH₃ | CH₃ | |
| NCH₃ | H | H | H | H | H | OCH₃ | OCH₃ | |
| NC₂H₅ | H | H | H | H | H | CH₃ | OCH₃ | |
| NC₂H₅ | H | H | H | H | H | CH₃ | CH₃ | |
| NC₂H₅ | H | H | H | H | H | OCH₃ | OCH₃ | |
| N—i-C₃H₇ | H | H | H | H | H | CH₃ | OCH₃ | |
| N—i-C₃H₇ | H | H | H | H | H | CH₃ | CH₃ | |
| N—i-C₃H₇ | H | H | H | H | H | OCH₃ | OCH₃ | |
| O | H | H | CH₃ | H | H | CH₃ | OCH₃ | |
| O | H | H | CH₃ | H | H | OCH₃ | OCH₃ | |
| O | H | H | CH₃ | H | H | CH₃ | CH₃ | |
| O | H | H | CH₃ | CH₃ | H | CH₃ | OCH₃ | |
| O | H | H | CH₃ | CH₃ | H | OCH₃ | OCH₃ | |
| O | H | H | CH₃ | CH₃ | H | CH₃ | CH₃ | |

TABLE IV

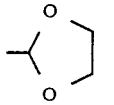

| Q | R₁ | R₂ | R₄ | R₅ | R | X | Y | m.p. (°C.) |
|---|---|---|---|---|---|---|---|---|
| O | H | H | H | H | H | CH₃ | OCH₃ | |
| O | H | H | H | H | H | OCH₃ | OCH₃ | |
| O | H | H | H | H | H | CH₃ | CH₃ | |
| O | H | H | H | H | H | C₂H₅ | OCH₃ | |
| O | H | H | H | H | H | OC₂H₅ | CH₃ | |
| O | H | H | H | H | H | OC₂H₅ | OCH₃ | |
| O | H | H | H | H | H | OCF₂H | CH₃ | |
| O | H | H | H | H | H | OCF₂H | OCH₃ | |
| O | H | H | H | H | H | OCF₂H | OCF₂H | |
| O | H | H | H | H | H | OCF₂H | CF₃ | |
| O | H | H | H | H | H | CF₃ | CF₃ | |
| O | H | H | H | H | H | CF₃ | OCH₃ | |
| O | H | H | H | H | H | CF₃ | OC₂H₅ | |
| O | H | H | H | H | H | OCH₃ | H | |
| O | H | H | H | H | H | OCH₃ | NH₂ | |
| O | H | H | H | H | H | OCH₃ | NHCH₃ | |
| O | H | H | H | H | H | OCH₃ | N(CH₃)₂ | |
| O | H | H | H | H | H | OCH₃ | n-C₄H₉ | |
| O | H | H | H | H | H | OCH₃ | CH₂OCH₃ | |
| O | H | H | H | H | H | OCH₃ | CH₂OC₂H₅ | |
| O | H | H | H | H | H | CH₃ | O—i-C₃H₇ | |
| O | H | H | H | H | H | CH₃ | O—n-C₄H₉ | |
| O | H | H | H | H | H | CH₃ | OCH₂CH=CH₂ | |
| O | H | H | H | H | H | CH₃ | OCH₂C≡CH | |
| O | H | H | H | H | H | CH₃ | OCH₂CH₂OCH₃ | |
| O | H | H | H | H | H | CH₃ | OCH₂CH₂F | |
| O | H | H | H | H | H | CH₃ | OCH₂CH₂Cl | |
| O | H | H | H | H | H | CH₃ | OCH₂CH₂Br | |
| O | H | H | H | H | H | CH₃ | CH(OCH₃)₂ | |
| O | H | H | H | H | H | CH₃ | CH(OC₂H₅)₂ | |
| O | H | H | H | H | H | CH₃ | OCH₂C(CH₃)=CH₂ | |
| O | H | H | H | H | H | CH₃ | OCH₂C≡CCH₃ | |
| O | H | H | H | H | H | OCH₃ | SCH₃ | |
| O | H | H | H | H | H | OCH₃ | SC₂H₅ | |
| O | H | H | H | H | H | OCH₃ | CH(OCH₃)₂ | |
| O | H | H | H | H | H | OCH₃ | CH(OC₂H₅)₂ | |
| O | H | H | H | H | H | OCH₃ | 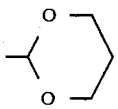 | |
| O | H | H | H | H | H | OCH₃ | CH₂Cl | |
| O | H | H | H | H | H | OCH₃ | SCF₂H | |
| O | H | H | H | H | H | CH₃ | OCF₂CF₂H | |
| O | H | H | H | H | H | CH₃ | OCF₂CHCF | |
| O | H | H | H | H | H | CH₃ | OCF₂CHBrF | |
| O | H | H | H | H | H | CH₃ | OCF₂CHFCF₃ | |
| O | H | H | H | H | H | CH₃ | OCH₂CF₃ | |
| O | CH₃ | H | H | H | H | OCH₃ | OCH₃ | |
| O | H | Cl | H | H | H | CH₃ | OCH₃ | |
| O | H | Br | H | H | H | CH₃ | OCH₃ | |
| O | H | OCH₃ | H | H | H | OCH₃ | OCH₃ | |
| O | H | OC₂H₅ | H | H | H | OCH₃ | OCH₃ | |
| O | H | O—n-C₃H₇ | H | H | H | OCH₃ | OCH₃ | |
| O | H | CF₃ | H | H | H | OCH₃ | OCH₃ | |
| O | H | H | H | H | CH₃ | OCH₃ | OCH₃ | |
| S | H | H | H | H | H | CH₃ | OCH₃ | |
| S | H | H | H | H | H | CH₃ | CH₃ | |
| S | H | H | H | H | H | OCH₃ | OCH₃ | |

TABLE IV-continued

| Q | R₁ | R₂ | R₄ | R₅ | R | X | Y | m.p. (°C.) |
|---|---|---|---|---|---|---|---|---|
| S | H | H | H | H | H | OCF₂H | OCH₃ | |
| S | H | H | H | H | H | CF₃ | OCH₃ | |
| S | H | H | H | H | H | OC₂H₅ | OCH₃ | |
| S | H | H | H | H | H | C₂H₅ | OCH₃ | |
| S | H | H | H | H | H | OCF₂H | OCF₂H | |
| S | H | H | H | H | H | CH₃ | OCF₂H | |
| S | H | H | H | H | H | OCH₃ | CH(OCH₃)₂ | |
| S | H | H | H | H | H | OCH₃ | SCH₃ | |
| S(O) | H | H | H | H | H | CH₃ | OCH₃ | |
| S(O) | H | H | H | H | H | CH₃ | CH₃ | |
| S(O) | H | H | H | H | H | OCH₃ | OCH₃ | |
| S(O) | H | H | H | H | H | OCF₂H | OCH₃ | |
| S(O) | H | H | H | H | H | CF₃ | OCH₃ | |
| S(O) | H | H | H | H | H | OC₂H₅ | OCH₃ | |
| S(O) | H | H | H | H | H | C₂H₅ | OCH₃ | |
| S(O) | H | H | H | H | H | OCF₂H | OCF₂H | |
| S(O) | H | H | H | H | H | CH₃ | OCF₂H | |
| S(O) | H | H | H | H | H | OCH₃ | CH(OCH₃)₂ | |
| SO₂ | H | H | H | H | H | CH₃ | OCH₃ | |
| SO₂ | H | H | H | H | H | CH₃ | CH₃ | |
| SO₂ | H | H | H | H | H | OCH₃ | OCH₃ | |
| SO₂ | H | H | H | H | H | OCF₂H | OCH₃ | |
| SO₂ | H | H | H | H | H | CF₃ | OCH₃ | |
| SO₂ | H | H | H | H | H | OC₂H₅ | OCH₃ | |
| SO₂ | H | H | H | H | H | C₂H₅ | OCH₃ | |
| SO₂ | H | H | H | H | H | OCF₂H | OCF₂H | |
| SO₂ | H | H | H | H | H | CH₃ | OCF₂H | |
| SO₂ | H | H | H | H | H | OCH₃ | CH(OCH₃)₂ | |
| SO₂ | H | H | H | H | H | OCH₃ | SCH₃ | |
| NH | H | H | H | H | H | CH₃ | OCH₃ | |
| NH | H | H | H | H | H | CH₃ | CH₃ | |
| NH | H | H | H | H | H | OCH₃ | OCH₃ | |
| NCH₃ | H | H | H | H | H | CH₃ | OCH₃ | |
| NCH₃ | H | H | H | H | H | CH₃ | CH₃ | |
| NCH₃ | H | H | H | H | H | OCH₃ | OCH₃ | |
| NC₂H₅ | H | H | H | H | H | CH₃ | OCH₃ | |
| NC₂H₅ | H | H | H | H | H | CH₃ | CH₃ | |
| NC₂H₅ | H | H | H | H | H | OCH₃ | OCH₃ | |
| N—i-C₃H₇ | H | H | H | H | H | CH₃ | OCH₃ | |
| N—i-C₃H₇ | H | H | H | H | H | CH₃ | CH₃ | |
| N—i-C₃H₇ | H | H | H | H | H | OCH₃ | OCH₃ | |
| O | H | H | CH₃ | H | H | OCH₃ | CH₃ | |
| O | H | H | CH₃ | H | H | OCH₃ | OCH₃ | |
| O | H | H | CH₃ | H | H | CH₃ | CH₃ | |
| O | H | H | CH₃ | CH₃ | H | OCH₃ | CH₃ | |
| O | H | H | CH₃ | CH₃ | H | OCH₃ | OCH₃ | |
| O | H | H | CH₃ | CH₃ | H | CH₃ | CH₃ | |

TABLE V

| Q | R₁ | R₂ | R₄ | R | X | Y | m.p. (°C.) |
|---|---|---|---|---|---|---|---|
| O | H | H | H | H | CH₃ | OCH₃ | |
| O | H | H | H | H | OCH₃ | OCH₃ | |

TABLE V-continued

[Structure: bicyclic aromatic with R4, Q, R1 substituents and SO2NHCON(R)- linked to pyrimidine bearing X and Y; H and R2 on the ring]

| Q | R₁ | R₂ | R₄ | R | X | Y | m.p. (°C.) |
|---|---|---|---|---|---|---|---|
| O | H | H | H | H | CH₃ | CH₃ | |
| O | H | H | H | H | C₂H₅ | OCH₃ | |
| O | H | H | H | H | OC₂H₅ | CH₃ | |
| O | H | H | H | H | OC₂H₅ | OCH₃ | |
| O | H | H | H | H | Cl | OCH₃ | |
| O | H | H | H | H | Br | OCH₃ | |
| O | H | H | H | H | F | OCH₃ | |
| O | H | H | H | H | OCF₂H | CH₃ | |
| O | H | H | H | H | OCF₂H | OCH₃ | |
| O | H | H | H | H | OCF₂H | OCF₂H | |
| O | H | H | H | H | OCF₂H | CF₃ | |
| O | H | H | H | H | CF₃ | CF₃ | |
| O | H | H | H | H | CF₃ | OCH₃ | |
| O | H | H | H | H | CF₃ | OC₂H₅ | |
| O | H | H | H | H | OCH₃ | H | |
| O | H | H | H | H | OCH₃ | NH₂ | |
| O | H | H | H | H | OCH₃ | NHCH₃ | |
| O | H | H | H | H | OCH₃ | N(CH₃)₂ | |
| O | H | H | H | H | OCH₃ | n-C₄H₉ | |
| O | H | H | H | H | OCH₃ | CH₂OCH₃ | |
| O | H | H | H | H | OCH₃ | CH₂OC₂H₅ | |
| O | H | H | H | H | CH₃ | O—i-C₃H₇ | |
| O | H | H | H | H | CH₃ | O—n-C₄H₉ | |
| O | H | H | H | H | CH₃ | OCH₂CH=CH₂ | |
| O | H | H | H | H | CH₃ | OCH₂C≡CH | |
| O | H | H | H | H | CH₃ | OCH₂CH₂OCH₃ | |
| O | H | H | H | H | CH₃ | OCH₂CH₂F | |
| O | H | H | H | H | CH₃ | OCH₂CH₂Cl | |
| O | H | H | H | H | CH₃ | OCH₂CH₂Br | |
| O | H | H | H | H | CH₃ | CH(OCH₃)₂ | |
| O | H | H | H | H | CH₃ | CH(OC₂H₅)₂ | |
| O | H | H | H | H | CH₃ | OCH₂C(CH₃)=CH₂ | |
| O | H | H | H | H | CH₃ | OCH₂C≡CCH₃ | |
| O | H | H | H | H | OCH₃ | SCH₃ | |
| O | H | H | H | H | OCH₃ | SC₂H₅ | |
| O | H | H | H | H | OCH₃ | CH(OCH₃)₂ | |
| O | H | H | H | H | OCH₃ | CH(OC₂H₅)₂ | |
| O | H | H | H | H | OCH₃ | [1,3-dioxolan-2-yl] | |
| O | H | H | H | H | OCH₃ | [1,3-dioxan-2-yl] | |
| O | H | H | H | H | OCH₃ | CH₂Cl | |
| O | H | H | H | H | OCH₃ | SCF₂H | |
| O | H | H | H | H | CH₃ | OCF₂CF₂H | |
| O | H | H | H | H | CH₃ | OCF₂CHCF | |
| O | H | H | H | H | CH₃ | OCF₂CHBrF | |
| O | H | H | H | H | CH₃ | OCF₂CHFCF₃ | |
| O | H | H | H | H | CH₃ | OCH₂CF₃ | |
| O | CH₃ | H | H | H | OCH₃ | OCH₃ | |
| O | H | Cl | H | H | CH₃ | OCH₃ | |
| O | H | Br | H | H | CH₃ | OCH₃ | |
| O | H | OCH₃ | H | H | OCH₃ | OCH₃ | |
| O | H | OC₂H₅ | H | H | OCH₃ | OCH₃ | |
| O | H | O—n-C₃H₇ | H | H | OCH₃ | OCH₃ | |
| O | H | CF₃ | H | H | OCH₃ | OCH₃ | |
| O | H | H | H | CH₃ | OCH₃ | OCH₃ | |
| S | H | H | H | H | CH₃ | OCH₃ | |
| S | H | H | H | H | CH₃ | CH₃ | |

TABLE V-continued

| Q | R₁ | R₂ | R₄ | R | X | Y | m.p. (°C.) |
|---|----|----|----|----|----|---|------------|
| S | H | H | H | H | OCH₃ | OCH₃ | |
| S | H | H | H | H | Cl | OCH₃ | |
| S | H | H | H | H | Br | OCH₃ | |
| S | H | H | H | H | F | OCH₃ | |
| S | H | H | H | H | OCF₂H | OCH₃ | |
| S | H | H | H | H | CF₃ | OCH₃ | |
| S | H | H | H | H | OC₂H₅ | OCH₃ | |
| S | H | H | H | H | C₂H₅ | OCH₃ | |
| S | H | H | H | H | OCF₂H | OCF₂H | |
| S | H | H | H | H | CH₃ | OCF₂H | |
| S | H | H | H | H | OCH₃ | CH(OCH₃)₂ | |
| S | H | H | H | H | OCH₃ | SCH₃ | |
| S(O) | H | H | H | H | CH₃ | OCH₃ | |
| S(O) | H | H | H | H | CH₃ | CH₃ | |
| S(O) | H | H | H | H | OCH₃ | OCH₃ | |
| S(O) | H | H | H | H | Cl | OCH₃ | |
| S(O) | H | H | H | H | Br | OCH₃ | |
| S(O) | H | H | H | H | F | OCH₃ | |
| S(O) | H | H | H | H | OCF₂H | OCH₃ | |
| S(O) | H | H | H | H | CF₃ | OCH₃ | |
| S(O) | H | H | H | H | OC₂H₅ | OCH₃ | |
| S(O) | H | H | H | H | C₂H₅ | OCH₃ | |
| S(O) | H | H | H | H | OCF₂H | OCF₂H | |
| S(O) | H | H | H | H | CH₃ | OCF₂H | |
| S(O) | H | H | H | H | OCH₃ | CH(OCH₃)₂ | |
| SO₂ | H | H | H | H | CH₃ | OCH₃ | |
| SO₂ | H | H | H | H | CH₃ | CH₃ | |
| SO₂ | H | H | H | H | OCH₃ | OCH₃ | |
| SO₂ | H | H | H | H | Cl | OCH₃ | |
| SO₂ | H | H | H | H | F | OCH₃ | |
| SO₂ | H | H | H | H | Br | OCH₃ | |
| SO₂ | H | H | H | H | OCF₂H | OCH₃ | |
| SO₂ | H | H | H | H | CF₃ | OCH₃ | |
| SO₂ | H | H | H | H | OC₂H₅ | OCH₃ | |
| SO₂ | H | H | H | H | C₂H₅ | OCH₃ | |
| SO₂ | H | H | H | H | OCF₂H | OCF₂H | |
| SO₂ | H | H | H | H | CH₃ | OCF₂H | |
| SO₂ | H | H | H | H | OCH₃ | CH(OCH₃)₂ | |
| SO₂ | H | H | H | H | OCH₃ | SCH₃ | |
| NH | H | H | H | H | CH₃ | OCH₃ | |
| NH | H | H | H | H | CH₃ | CH₃ | |
| NH | H | H | H | H | OCH₃ | OCH₃ | |
| NCH₃ | H | H | H | H | CH₃ | OCH₃ | |
| NCH₃ | H | H | H | H | CH₃ | CH₃ | |
| NCH₃ | H | H | H | H | OCH₃ | OCH₃ | |
| NC₂H₅ | H | H | H | H | CH₃ | OCH₃ | |
| NC₂H₅ | H | H | H | H | CH₃ | CH₃ | |
| NC₂H₅ | H | H | H | H | OCH₃ | OCH₃ | |
| N—i-C₃H₇ | H | H | H | H | CH₃ | OCH₃ | |
| N—i-C₃H₇ | H | H | H | H | CH₃ | CH₃ | |
| N—i-C₃H₇ | H | H | H | H | OCH₃ | OCH₃ | |
| O | H | H | CH₃ | H | OCH₃ | CH₃ | |
| O | H | H | CH₃ | H | OCH₃ | OCH₃ | |
| O | H | H | CH₃ | H | CH₃ | CH₃ | |

TABLE VI

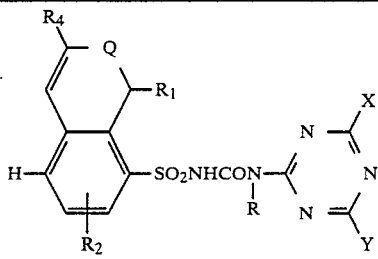

| Q | R₁ | R₂ | R₄ | R | X | Y | m.p. (°C.) |
|---|----|----|----|----|------|------|-----|
| O | H | H | H | H | CH₃ | OCH₃ | |
| O | H | H | H | H | OCH₃ | OCH₃ | |
| O | H | H | H | H | CH₃ | CH₃ | |
| O | H | H | H | H | C₂H₅ | OCH₃ | |
| O | H | H | H | H | OC₂H₅ | CH₃ | |
| O | H | H | H | H | OC₂H₅ | OCH₃ | |
| O | H | H | H | H | OCF₂H | CH₃ | |
| O | H | H | H | H | OCF₂H | OCH₃ | |
| O | H | H | H | H | OCF₂H | OCF₂H | |
| O | H | H | H | H | OCF₂H | CF₃ | |
| O | H | H | H | H | CF₃ | CF₃ | |
| O | H | H | H | H | CF₃ | OCH₃ | |
| O | H | H | H | H | CF₃ | OC₂H₅ | |
| O | H | H | H | H | OCH₃ | H | |
| O | H | H | H | H | OCH₃ | NH₂ | |
| O | H | H | H | H | OCH₃ | NHCH₃ | |
| O | H | H | H | H | OCH₃ | N(CH₃)₂ | |
| O | H | H | H | H | OCH₃ | n-C₄H₉ | |
| O | H | H | H | H | OCH₃ | CH₂OCH₃ | |
| O | H | H | H | H | OCH₃ | CH₂OC₂H₅ | |
| O | H | H | H | H | CH₃ | O—i-C₃H₇ | |
| O | H | H | H | H | CH₃ | O—n-C₄H₉ | |
| O | H | H | H | H | CH₃ | OCH₂CH=CH₂ | |
| O | H | H | H | H | CH₃ | OCH₂C≡CH | |
| O | H | H | H | H | CH₃ | OCH₂CH₂OCH₃ | |
| O | H | H | H | H | CH₃ | OCH₂CH₂F | |
| O | H | H | H | H | CH₃ | OCH₂CH₂Cl | |
| O | H | H | H | H | CH₃ | OCH₂CH₂Br | |
| O | H | H | H | H | CH₃ | CH(OCH₃)₂ | |
| O | H | H | H | H | CH₃ | CH(OC₂H₅)₂ | |
| O | H | H | H | H | CH₃ | OCH₂C(CH₃)=CH₂ | |
| O | H | H | H | H | CH₃ | OCH₂C≡CCH₃ | |
| O | H | H | H | H | OCH₃ | SCH₃ | |
| O | H | H | H | H | OCH₃ | SC₂H₅ | |
| O | H | H | H | H | OCH₃ | CH(OCH₃)₂ | |
| O | H | H | H | H | OCH₃ | CH(OC₂H₅)₂ | |
| O | H | H | H | H | OCH₃ | (1,3-dioxolan-2-yl) | |
| O | H | H | H | H | OCH₃ | (1,3-dioxan-2-yl) | |
| O | H | H | H | H | OCH₃ | CH₂Cl | |
| O | H | H | H | H | OCH₃ | SCF₂H | |
| O | H | H | H | H | CH₃ | OCF₂CF₂H | |
| O | H | H | H | H | CH₃ | OCF₂CHCF | |
| O | H | H | H | H | CH₃ | OCF₂CHBrF | |
| O | H | H | H | H | CH₃ | OCF₂CHFCF₃ | |
| O | H | H | H | H | CH₃ | OCH₂CF₃ | |
| O | CH₃ | H | H | H | OCH₃ | OCH₃ | |
| O | H | Cl | H | H | CH₃ | OCH₃ | |
| O | H | Br | H | H | CH₃ | OCH₃ | |
| O | H | OCH₃ | H | H | OCH₃ | OCH₃ | |
| O | H | OC₂H₅ | H | H | OCH₃ | OCH₃ | |
| O | H | O—n-C₃H₇ | H | H | OCH₃ | OCH₃ | |
| O | H | CF₃ | H | H | OCH₃ | OCH₃ | |
| O | H | H | H | CH₃ | OCH₃ | OCH₃ | |
| S | H | H | H | H | CH₃ | OCH₃ | |
| S | H | H | H | H | CH₃ | CH₃ | |
| S | H | H | H | H | OCH₃ | OCH₃ | |

TABLE VI-continued

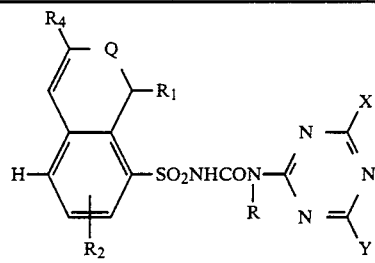

| Q | R₁ | R₂ | R₄ | R | X | Y | m.p. (°C.) |
|---|----|----|----|----|----|----|----|
| S | H | H | H | H | OCF₂H | OCH₃ | |
| S | H | H | H | H | CF₃ | OCH₃ | |
| S | H | H | H | H | OC₂H₅ | OCH₃ | |
| S | H | H | H | H | C₂H₅ | OCH₃ | |
| S | H | H | H | H | OCF₂H | OCF₂H | |
| S | H | H | H | H | CH₃ | OCF₂H | |
| S | H | H | H | H | OCH₃ | CH(OCH₃)₂ | |
| S | H | H | H | H | OCH₃ | SCH₃ | |
| S(O) | H | H | H | H | CH₃ | OCH₃ | |
| S(O) | H | H | H | H | CH₃ | CH₃ | |
| S(O) | H | H | H | H | OCH₃ | OCH₃ | |
| S(O) | H | H | H | H | OCF₂H | OCH₃ | |
| S(O) | H | H | H | H | CF₃ | OCH₃ | |
| S(O) | H | H | H | H | OC₂H₅ | OCH₃ | |
| S(O) | H | H | H | H | C₂H₅ | OCH₃ | |
| S(O) | H | H | H | H | OCF₂H | OCF₂H | |
| S(O) | H | H | H | H | CH₃ | OCF₂H | |
| S(O) | H | H | H | H | OCH₃ | CH(OCH₃)₂ | |
| SO₂ | H | H | H | H | CH₃ | OCH₃ | |
| SO₂ | H | H | H | H | CH₃ | CH₃ | |
| SO₂ | H | H | H | H | OCH₃ | OCH₃ | |
| SO₂ | H | H | H | H | OCF₂H | OCH₃ | |
| SO₂ | H | H | H | H | CF₃ | OCH₃ | |
| SO₂ | H | H | H | H | OC₂H₅ | OCH₃ | |
| SO₂ | H | H | H | H | C₂H₅ | OCH₃ | |
| SO₂ | H | H | H | H | OCF₂H | OCF₂H | |
| SO₂ | H | H | H | H | CH₃ | OCF₂H | |
| SO₂ | H | H | H | H | OCH₃ | CH(OCH₃)₂ | |
| SO₂ | H | H | H | H | OCH₃ | SCH₃ | |
| NH | H | H | H | H | CH₃ | OCH₃ | |
| NH | H | H | H | H | CH₃ | CH₃ | |
| NH | H | H | H | H | OCH₃ | OCH₃ | |
| NCH₃ | H | H | H | H | CH₃ | OCH₃ | |
| NCH₃ | H | H | H | H | CH₃ | CH₃ | |
| NCH₃ | H | H | H | H | OCH₃ | OCH₃ | |
| NC₂H₅ | H | H | H | H | CH₃ | OCH₃ | |
| NC₂H₅ | H | H | H | H | CH₃ | CH₃ | |
| NC₂H₅ | H | H | H | H | OCH₃ | OCH₃ | |
| N—i-C₃H₇ | H | H | H | H | CH₃ | OCH₃ | |
| N—i-C₃H₇ | H | H | H | H | CH₃ | CH₃ | |
| N—i-C₃H₇ | H | H | H | H | OCH₃ | OCH₃ | |
| O | H | H | CH₃ | H | OCH₃ | OCH₃ | |
| O | H | H | CH₃ | H | OCH₃ | OCH₃ | |
| O | H | H | CH₃ | H | CH₃ | CH₃ | |

TABLE VII

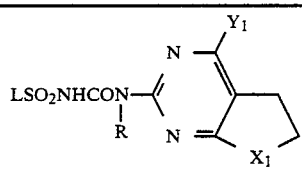

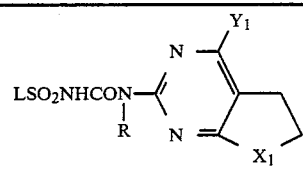

| L | Q | R₁ | R₂ | R₄ | R₅ | R | X₁ | Y₁ | L | Q | R₁ | R₂ | R₄ | R₅ | R | X₁ | Y₁ |
|---|---|----|----|----|----|----|----|----|---|---|----|----|----|----|----|----|----|
| L-1 | O | H | H | — | — | H | CH₂ | H | L-1 | S | H | H | — | — | H | CH₂ | CH₃ |
| L-1 | O | H | H | — | — | H | CH₂ | CH₃ | L-1 | S | H | H | — | — | H | CH₂ | OCH₃ |
| L-1 | O | H | H | — | — | H | CH₂ | OCH₃ | L-1 | S | H | H | — | — | H | CH₂ | Cl |
| L-1 | O | H | H | — | — | H | CH₂ | Cl | L-1 | S | H | H | — | — | H | O | H |
| L-1 | O | CH₃ | H | — | — | H | CH₂ | OCH₃ | L-1 | S | H | H | — | — | H | O | CH₃ |
| L-1 | O | H | H | — | — | H | O | H | L-1 | S | H | H | — | — | H | O | OCH₃ |
| L-1 | O | H | Cl | — | — | H | O | CH₃ | L-1 | S | H | H | — | — | H | O | Cl |
| L-1 | O | H | H | — | — | H | O | OCH₃ | L-1 | S(O) | H | H | — | — | H | CH₂ | H |
| L-1 | O | H | H | — | — | H | O | Cl | L-1 | S(O) | H | H | — | — | H | CH₂ | CH₃ |
| L-1 | S | H | H | — | — | H | CH₂ | H | L-1 | S(O) | H | H | — | — | H | CH₂ | OCH₃ |

TABLE VII-continued

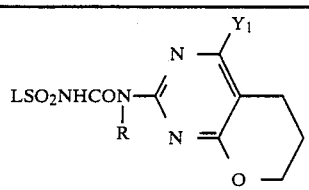

| L | Q | R₁ | R₂ | R₄ | R₅ | R | X₁ | Y₁ |
|---|---|---|---|---|---|---|---|---|
| L-1 | S(O) | H | H | — | — | H | CH₂ | Cl |
| L-1 | S(O) | H | H | — | — | H | O | H |
| L-1 | S(O) | H | H | — | — | H | O | CH₃ |
| L-1 | S(O) | H | H | — | — | H | O | OCH₃ |
| L-1 | S(O) | H | H | — | — | H | O | Cl |
| L-1 | SO₂ | H | H | — | — | H | CH₂ | H |
| L-1 | SO₂ | H | H | — | — | H | CH₂ | CH₃ |
| L-1 | SO₂ | H | H | — | — | H | CH₂ | OCH₃ |
| L-1 | SO₂ | H | H | — | — | H | CH₂ | Cl |
| L-1 | SO₂ | H | H | — | — | H | O | H |
| L-1 | SO₂ | H | H | — | — | H | O | CH₃ |
| L-1 | SO₂ | H | H | — | — | H | O | OCH₃ |
| L-1 | SO₂ | H | H | — | — | H | O | Cl |
| L-1 | NCH₃ | H | H | — | — | H | CH₂ | H |
| L-1 | NCH₃ | H | H | — | — | H | CH₂ | CH₃ |
| L-1 | NCH₃ | H | H | — | — | H | CH₂ | OCH₃ |
| L-1 | NCH₃ | H | H | — | — | H | CH₂ | Cl |
| L-1 | NCH₃ | H | H | — | — | H | O | H |
| L-1 | NCH₃ | H | H | — | — | H | O | CH₃ |
| L-1 | NCH₃ | H | H | — | — | H | O | OCH₃ |
| L-1 | NCH₃ | H | H | — | — | H | O | Cl |
| L-2 | O | H | H | H | H | H | CH₂ | OCH₃ |
| L-2 | O | H | H | H | H | H | O | OCH₃ |
| L-2 | S | H | H | H | H | H | CH₂ | CH₃ |
| L-2 | S | H | H | H | H | H | O | OCH₃ |
| L-2 | SO₂ | H | H | H | H | H | CH₂ | OCH₃ |
| L-2 | SO₂ | H | H | H | H | H | O | CH₃ |
| L-2 | NCH₃ | H | H | H | H | H | O | CH₃ |
| L-3 | O | H | H | H | — | H | O | CH₃ |
| L-3 | S | H | H | H | — | H | CH₂ | CH₃ |
| L-3 | SO₂ | H | H | H | — | H | O | CH₃ |
| L-3 | NCH₃ | H | H | H | — | H | O | CH₃ |
| L-1 | O | H | H | — | — | CH₃ | O | CH₃ |

TABLE VIII

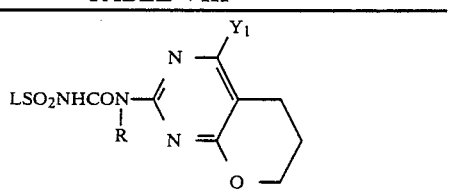

| L | Q | R₁ | R₂ | R₄ | R₅ | R | Y₁ |
|---|---|---|---|---|---|---|---|
| L-1 | O | H | OCH₃ | — | — | H | CH₃ |
| L-1 | O | H | H | — | — | H | OCH₃ |
| L-1 | O | H | H | — | — | H | CH₃ |
| L-1 | O | H | H | — | — | H | Cl |
| L-1 | S | H | H | — | — | H | H |
| L-1 | S | H | H | — | — | H | CH₃ |
| L-1 | S | H | H | — | — | CH₃ | OCH₃ |
| L-1 | S | H | H | — | — | H | Cl |
| L-1 | S(O) | H | H | — | — | H | OCH₃ |
| L-1 | SO₂ | H | H | — | — | H | H |
| L-1 | SO₂ | H | H | — | — | H | Cl |
| L-1 | SO₂ | H | H | — | — | H | CH₃ |
| L-1 | SO₂ | H | H | — | — | H | OCH₃ |
| L-1 | NCH₃ | H | H | — | — | H | H |
| L-1 | NCH₃ | H | H | — | — | H | Cl |
| L-1 | NCH₃ | H | H | — | — | H | CH₃ |
| L-1 | NCH₃ | H | H | — | — | H | OCH₃ |
| L-2 | O | H | H | H | H | H | OCH₃ |
| L-2 | S | H | H | H | H | H | OCH₃ |
| L-2 | SO₂ | H | H | H | H | H | OCH₃ |
| L-2 | CH₃ | H | H | H | H | H | OCH₃ |
| L-3 | O | H | H | H | — | H | OCH₃ |
| L-3 | S | H | H | H | — | H | OCH₃ |
| L-3 | SO₂ | H | H | H | — | H | OCH₃ |

TABLE VIII-continued

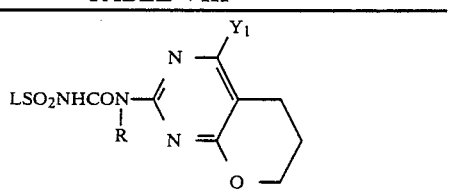

| L | Q | R₁ | R₂ | R₄ | R₅ | R | Y₁ |
|---|---|---|---|---|---|---|---|
| L-3 | NCH₃ | H | H | H | — | H | OCH₃ |

TABLE IX

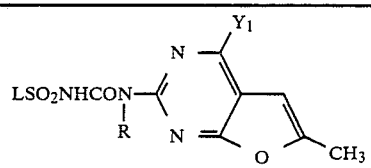

| L | Q | R₁ | R₂ | R₄ | R₅ | R | Y₁ |
|---|---|---|---|---|---|---|---|
| L-1 | O | H | CH₃ | — | — | H | OCH₃ |
| L-1 | O | CH₃ | H | — | — | H | OCH₃ |
| L-1 | O | H | H | — | — | CH₃ | OCH₃ |
| L-1 | O | H | H | — | — | H | H |
| L-1 | O | H | H | — | — | H | Cl |
| L-1 | O | H | H | — | — | H | OCH₃ |
| L-1 | O | H | H | — | — | H | CH₃ |
| L-1 | S | H | H | — | — | H | H |
| L-1 | S | H | H | — | — | H | Cl |
| L-1 | S | H | H | — | — | H | CH₃ |
| L-1 | S | H | H | — | — | H | OCH₃ |
| L-1 | S(O) | H | H | — | — | H | H |
| L-1 | S(O) | H | H | — | — | H | Cl |
| L-1 | S(O) | H | H | — | — | H | CH₃ |
| L-1 | S(O) | H | H | — | — | H | OCH₃ |
| L-1 | SO₂ | H | H | — | — | H | H |
| L-1 | SO₂ | H | H | — | — | H | Cl |
| L-1 | SO₂ | H | H | — | — | H | CH₃ |
| L-1 | SO₂ | H | H | — | — | H | OCH₃ |
| L-1 | NCH₃ | H | H | — | — | H | H |
| L-1 | NCH₃ | H | H | — | — | H | Cl |
| L-1 | NCH₃ | H | H | — | — | H | CH₃ |
| L-1 | NCH₃ | H | H | — | — | H | OCH₃ |
| L-2 | O | H | H | H | H | H | OCH₃ |
| L-3 | SO₂ | H | H | H | — | H | OCH₃ |

TABLE X

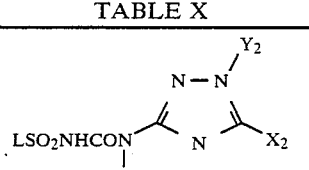

| L | Q | R₁ | R₂ | R₄ | R₅ | R | X₂ | Y₂ |
|---|---|---|---|---|---|---|---|---|
| L-1 | O | H | H | — | — | H | CH₃ | SCH₃ |
| L-1 | O | H | H | — | — | H | CH₃ | OCH₃ |
| L-1 | O | H | H | — | — | H | CH₃ | CH₃ |
| L-1 | O | H | H | — | — | H | C₂H₅ | OCH₃ |
| L-1 | O | H | H | — | — | H | CH₂CF₃ | OCH₃ |
| L-1 | S | H | H | — | — | H | CH₃ | SCH₃ |
| L-1 | S | H | H | — | — | H | CH₃ | OCH₃ |
| L-1 | S | H | H | — | — | H | CH₃ | CH₃ |
| L-1 | SO₂ | H | H | — | — | H | CH₃ | SCH₃ |
| L-1 | SO₂ | H | H | — | — | H | CH₃ | OCH₃ |
| L-1 | SO₂ | H | H | — | — | H | CH₃ | CH₃ |
| L-1 | NCH₃ | H | H | — | — | H | CH₃ | CH₃ |
| L-1 | NCH₃ | H | H | — | — | H | CH₃ | SCH₃ |
| L-1 | NCH₃ | H | H | — | — | H | CH₃ | OCH₃ |
| L-2 | O | H | H | H | H | H | CH₃ | OCH₃ |
| L-2 | O | H | H | H | H | H | CH₃ | SCH₃ |
| L-2 | S | H | H | H | H | H | CH₃ | OCH₃ |

TABLE X-continued $$\text{LSO}_2\text{NHCON} \overset{\overset{\displaystyle Y_2}{\underset{\displaystyle |}{N-N}}}{\underset{\displaystyle R}{\diagdown}} \overset{\displaystyle N}{\diagup} X_2$$

| L | Q | R₁ | R₂ | R₄ | R₅ | R | X₂ | Y₂ |
|---|---|---|---|---|---|---|---|---|
| L-2 | S | H | H | H | H | H | CH₃ | SCH₃ |
| L-2 | SO₂ | H | H | H | H | H | CH₃ | OCH₃ |
| L-2 | NCH₃ | H | H | H | H | H | CH₃ | OCH₃ |
| L-3 | O | H | H | H | — | H | CH₃ | OCH₃ |
| L-3 | S | H | H | H | — | H | CH₃ | OCH₃ |
| L-3 | SO₂ | H | H | H | — | H | CH₃ | OCH₃ |
| L-3 | NCH₃ | H | H | H | — | H | CH₃ | OCH₃ |

TABLE XI $$\text{LSO}_2\text{NHCONCH}_2 \diagup \bigcirc \overset{\overset{\displaystyle N \diagup X_3}{}}{\underset{\displaystyle N \diagdown OCH_3}{}}$$

| L | Q | R₁ | R₂ | R₄ | R₅ | R | Y₂ |
|---|---|---|---|---|---|---|---|
| L-1 | O | H | H | — | — | H | OCH₃ |
| L-1 | O | H | H | — | — | H | CH₃ |
| L-1 | S | H | H | — | — | H | OCH₃ |
| L-1 | S | H | H | — | — | H | CH₃ |
| L-1 | SO₂ | H | H | — | — | H | OCH₃ |
| L-1 | SO₂ | H | H | — | — | H | CH₃ |
| L-1 | NCH₃ | H | H | — | — | H | OCH₃ |
| L-1 | NCH₃ | H | H | — | — | H | CH₃ |
| L-2 | O | H | H | H | H | H | OCH₃ |
| L-2 | S | H | H | H | H | H | OCH₃ |
| L-2 | SO₂ | H | H | H | H | H | OCH₃ |
| L-2 | NCH₃ | H | H | H | H | H | OCH₃ |
| L-3 | O | H | H | H | — | H | OCH₃ |
| L-3 | S | H | H | H | — | H | OCH₃ |
| L-3 | SO₂ | H | H | H | — | H | OCH₃ |
| L-3 | NCH₃ | H | H | H | — | H | OCH₃ |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE XII

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy will. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE 18

Wettable Powder

| | |
|---|---|
| 1,3-Dihydro-N—[(4-methoxy-6-methylpyrimidin-2-yl)-aminocarbonyl]benzo[c]furan-4-sulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 19

Wettable Powder

| | |
|---|---|
| 1,3-Dihydro-N—[(4-methoxy-6-methylpyrimidin-2-yl)-aminocarbonyl]benzo[c]furan-4-sulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 20

Granule

| | |
|---|---|
| Wettable Powder of Example 19 | 5% |
| attapulgite granules (U.S.S. 20–40 mesh; 0.84–0.42 mm) | 95% |

A slurry of wettable powder containing ≈25% solids is sprayed on the surface of attapulgite granules while tumbling in a double-cone blender. The granules are dried and packaged.

EXAMPLE 21

Extruded Pellet

| | |
|---|---|
| 1,3-Dihydro-N—[(4,6-dimethoxypyrimidin-2-yl)aminocarbonyl]benzo[c]furan-4-sulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 22

Oil Suspension

| | |
|---|---|
| 1,3-Dihydro-N—[(4-methoxy-6-methyl-1,3,5-triazin-2-yl)-aminocarbonyl]benzo[c]furan-4-sulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 23

Wettable Powder

| | |
|---|---|
| 1,3-Dihydro-N—[(4,6-dimethoxy-1,3,5-triazin-2-yl)-aminocarbonyl]benzo[c]furan-4-sulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 24

Low Strength Granule

| | |
|---|---|
| 1,3-Dihydro-N—[(4,6-dimethoxypyrimidin-2-yl)aminocarbonyl]benzo[c]furan-4-sulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 25

Aqueous Suspension

| | |
|---|---|
| 1,3-Dihydro-N—[(4-methoxy-6-methyl-1,3,5-triazin-2-yl)-aminocarbonyl]benzo[c]furan-4-sulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 26

Solution

| | |
|---|---|
| 1,3-Dihydro-N—[(4,6-dimethoxy-1,3,5-triazin-2-yl)-aminocarbonyl]benzo[c]furan-4-sulfonamide, sodium salt | 5% |
| water | 95% |

The salt is added directly to the water with stirring to produce the solution, which may then be packaged for use.

EXAMPLE 27

Low Strength Granule

| | |
|---|---|
| 1,3-Dihydro-N—[(4-methoxy-6-methyl-1,3,5-triazin-2-yl)-aminocarbonyl]benzo[c]furan-4-sulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 28

Granule

| | |
|---|---|
| 1,3-Dihydro-N—[(4,6-dimethoxy-1,3,5-triazin-2-yl)-aminocarbonyl]benzo[c]furan-4-sulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 29

High Strength Concentrate

| | |
|---|---|
| 1,3-Dihydro-N—[(4,6-dimethoxypyrimidin-2-yl)aminocarbonyl]benzo[c]furan-4-sulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 30

Wettable Powder

| | |
|---|---|
| 1,3-Dihydro-N—[(4,6-dimethoxy-1,3,5-triazin-2-yl)-aminocarbonyl]benzo[c]furan-4-sulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 31

Wettable Powder

| | |
|---|---|
| 1,3-Dihydro-N—[(4-methoxy-6-methyl-1,3,5-triazin-2-yl)-aminocarbonyl]benzo[c]furan-4-sulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 32

Oil Suspension

| | |
|---|---|
| 1,3-Dihydro-N—[(4-methoxy-6-methylpyrimidin-2-yl)-aminocarbonyl]benzo[c]furan-4-sulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

UTILITY

Test results indicate that the compounds of the present invention are active herbicides. They should have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, many of the subject compounds should be useful for the selective post-emergence weed control in crops, especially wheat.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.005 to 10 kg/ha, the lower rates being suggested for use on lighter soils and/or those having a low organic matter content, for selective weed control or for situations where only short-term persistence is required.

The compounds of the invention may be used in combination with any other commercial herbicide; examples of which are those of the triazine, triazole, uracil, urea, amide, diphenylether, carbamate and bipyridylium types.

The herbicidal properties of the subject compounds were discovered in a greenhouse test. The test procedure and results follow.

TEST A

Seeds of crabgrass (*Digitaria* sp.), barnyardgrass (*Echinochloa crusgalli*), wild oats (*Avena fatua*), sicklepod (*Cassia obtusifolia*), morningglory (*Ipomoea* sp.), cocklebur (*Xanthium* sp.), sorghum, corn, soybean, sugar beet, cotton, rice, wheat and purple nutsedge (*Cyperus rotundus*) tubers were planted and treated pre-emergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
E=emergence inhibition;
G=growth retardation;
H=formative effects; and
U=unusual pigmentation.

It will be seen from the data for some of the compounds tested that wheat is tolerant of rates of application which provide excellent control of several problem weed species. Therefore, compounds from within the scope of the invention should be useful for selective post-emergence weed control in cereal crops, such as wheat.

Structures

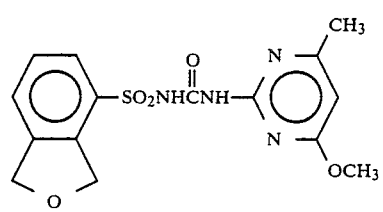
Compound 1

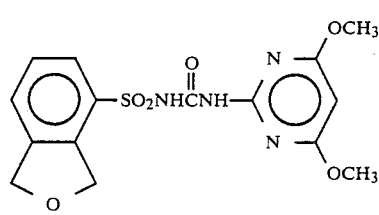
Compound 2

-continued
Structures

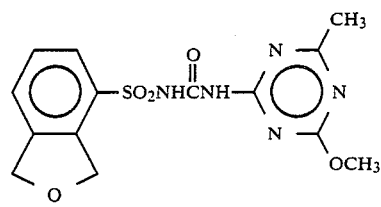
Compound 3

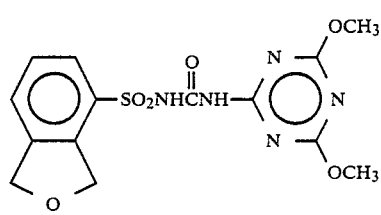
Compound 4

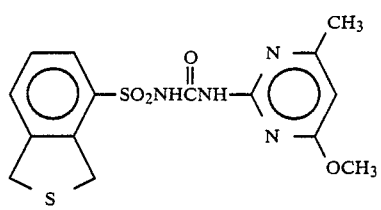
Compound 5

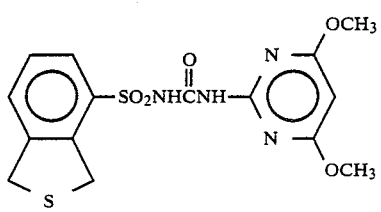
Compound 6

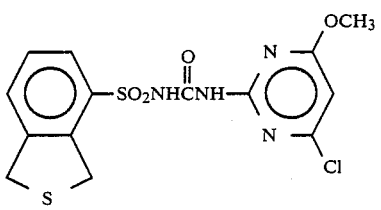
Compound 7

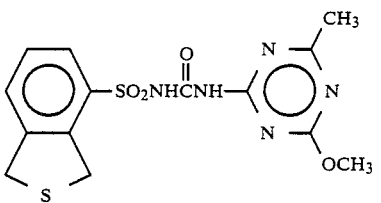
Compound 8

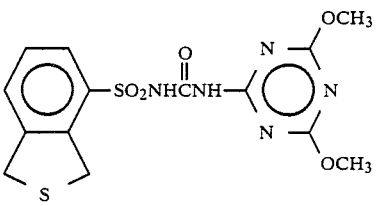
Compound 9

-continued
Structures

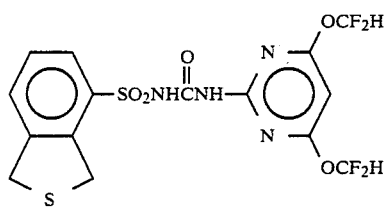
Compound 10

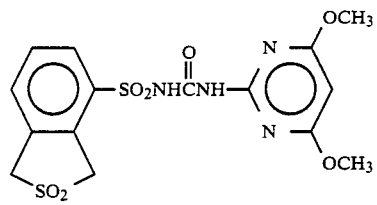
Compound 11

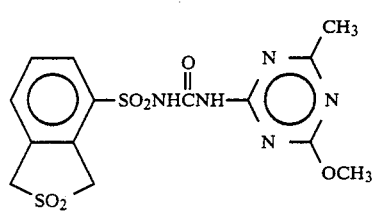
Compound 12 where

L is 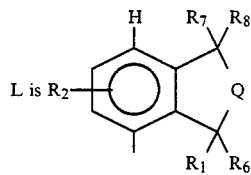 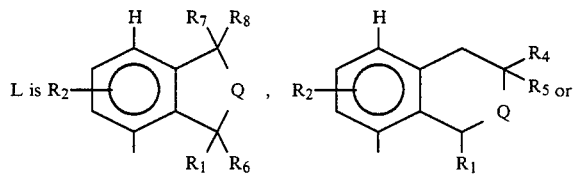

L-1 , L-2

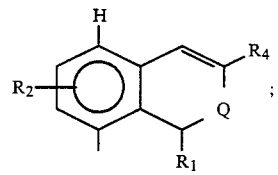

L-3

Q is O, S(O)$_n$ or NR$_3$;
n is 0, 1 or 2;
R$_1$ is H, CH$_3$, Cl or F;
R$_2$ is H, Cl, Br, C$_1$-C$_3$ alkoxy or CF$_3$;
R$_3$ is H or C$_1$-C$_4$ alkyl;
R$_4$ is H or CH$_3$;
R$_5$ is H or CH$_3$;
R$_6$ is H, Cl or F;

TABLE A

| Rate g/ha | Cmpd. 1 50 | Cmpd. 2 50 | Cmpd. 3 50 | Cmpd. 4 50 | Cmpd. 5 50 | Cmpd. 6 50 | Cmpd. 7 50 | Cmpd. 8 50 | Cmpd. 9 50 | Cmpd. 10 50 | Cmpd. 11 50 | Cmpd. 12 50 |
|---|---|---|---|---|---|---|---|---|---|---|---|---|
| POST-EMERGENCE |
| Morningglory | 6C,9G | 5C,9G | 9C | 4C,8H | 2C,5G | 2C,6G | 2G | 2G | 0 | 2G | 3C,7H | 0 |
| Cocklebur | 9C | 2C,8H | 10C | 8H | 3C,9H | 3C,8H | 2C,6G | 2C,9H | 1C,3G | 2G | 3C,9H | 0 |
| Sicklepod | 9C | 7G | 5C,9G | 4C,8H | 2C,2G | 2C | 1C | 1C | 0 | 0 | 3C,7G | 0 |
| Nutsedge | 9C | 4C,9G | 5G | 4G | 2C,8G | 2C,8G | 0 | 0 | 0 | 0 | 0 | 0 |
| Crabgrass | 8G | 5H | 2C,7G | 3G | 2C | 0 | 0 | 2G | 0 | 0 | 0 | 0 |
| Barnyardgrass | 4C,9H | 2C,9H | 6C,9H | 9H | 5C,9H | 3C,8H | 0 | 2C,8H | 0 | 0 | 0 | 0 |
| Wild Oats | 5C,9G | 2G | 4C,9G | 0 | 0 | 0 | 0 | 1C | 0 | 0 | 0 | 0 |
| Wheat | 9C | 2G | 6C,9G | 0 | 0 | 0 | 0 | 1C | 0 | 0 | 0 | 0 |
| Corn | 5U,9C | 2C,9H | 6U,9G | 7H | 1C,9G | 3C,7H | 2C,7H | 2C,9H | 1C,1H | 0 | 0 | 0 |
| Soybean | 5C,9G | 5C,9G | 9C | 6C,9G | 3C,8G | 2C,8G | 1C,1H | 2C,8G | 1C,5G | 0 | 2C,9G | 0 |
| Rice | 6C,9G | 2C,5G | 9C | 6C,9G | 2C,5G | 2C,5G | 2G | 2C,8G | 7G | 0 | 0 | 0 |
| Sorghum | 2C,9H | 2C,6H | 7U,9G | 9G | 2C,9G | 2C,6H | 2G | 2C,8H | 2C,8H | 0 | 3C,9H | 0 |
| Sugar beet | 9C | 9C | 9C | 3C,6H | 3C,8H | 3C,8G | 6G | 3C,9G | 2C,8G | 1C | 9C | 0 |
| Cotton | 4C,9G | 3C,9G | 9C | 5C,9G | 4C,8H | 3C,9G | 2G | 1C | 5G | 0 | 4C,9H | 0 |
| PRE-EMERGENCE |
| Morningglory | 9G | 9G | 9G | 9H | 8G | 2C,7G | — | 6G | 3C,6H | 0 | 3C,8G | 0 |
| Cocklebur | 9H | 9H | 9H | 9H | 9G | 9G | 4G | 1H | 9H | 0 | 2C,2H | 0 |
| Sicklepod | 9G | 9G | 9G | 9G | 8G | 8G | 0 | 8G | 2C,8G | 0 | 3C,7G | 0 |
| Nutsedge | 10E | 10E | 7G | 7G | 2G | 10E | 0 | 0 | 0 | 0 | 5G | 0 |
| Crabgrass | 4C,9G | 4C,9G | 5C,9G | 3C,7G | 0 | 0 | 0 | 0 | 0 | 0 | 0 | 0 |
| Barnyardgrass | 5C,9H | 9H | 5C,9H | 3C,9H | 5G | 2C,5G | 0 | 3G | 1H | 0 | 2C,4G | 0 |
| Wild Oats | 5C,9H | 4C,9G | 4C,9G | 2C,9G | 2C,9G | 4G | 0 | 0 | 0 | 0 | 4G | 0 |
| Wheat | 7C,9H | 4C,9G | 5C,9G | 8G | 0 | 0 | 0 | 0 | 0 | 0 | 0 | 0 |
| Corn | 10E | 2U,9G | 3U,9G | 4C,9G | 2C,9G | 2C,8H | 2G | 6G | 4G | 0 | 2C,7G | 0 |
| Soybean | 9H | 3C,8H | 9H | 4C,8H | 2C,6G | 2C,6G | 0 | 2C,5G | 1C | 0 | 3C,4H | 2C |
| Rice | 10E | 10E | 10E | 10E | 3C,6G | 3C,8G | 2C | 3C,5G | 2C,5G | 0 | 3C,6G | 0 |
| Sorghum | 10H | 2U,9G | 6C,9H | 2C,9H | 3C,8G | 3C,9H | 2C,3G | 3C,8G | 2C,5G | 0 | 3C,9H | 0 |
| Sugar beet | 10E | 10E | 9G | 9G | 2C,9G | 3C,9G | 6G | 8H | 7G | 0 | 9C | 0 |
| Cotton | 9G | 9G | 9G | 9G | 8G | 8G | 2G | 1C | 7G | 0 | 8H | 0 |

What is claimed is:

1. A compound having the formula:

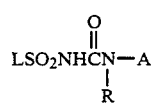

R$_7$ is H, Cl or F;
R$_8$ is H, Cl or F;
R is H or CH$_3$;
A is

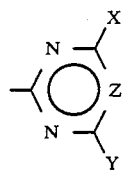 A-1

X is F, Cl, Br, $C_1$–$C_2$ alkyl, $C_1$–$C_2$ alkoxy, $OCF_2H$ or $CF_3$;

Y is H, $NH_2$, $NHCH_3$, $N(CH_3)_2$, $C_1$–$C_4$ alkyl, $C_1$–$C_4$ alkyl substituted with 1–3 atoms of (a) F, (b) Cl or (c) Br, $CH_2OCH_3$, $CH_2OC_2H_5$, $C_1$–$C_4$ alkoxy, $C_1$–$C_2$ alkylthio, $C_3$–$C_4$ alkenyloxy, $C_3$–$C_4$ alkynyloxy, $OCH_2CH_2OCH_3$, $OCH_2CH_2F$, $OCH_2CH_2Cl$, $OCH_2CH_2Br$, $OCH_2CF_3$, $CH(OCH_3)_2$, $CH(OC_2H_5)_2$,

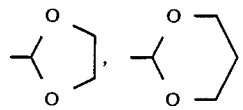

or $GCF_2T$;

G is O or S;

T is H, CHClF, CHBrF, $CF_2H$ or $CHFCF_3$;

Z is CH;

provided that:
(1) when X is F, Cl or Br, then Y is $NH_2$, $NHCH_3$, $N(CH_3)_2$, $CH_3$, $OCH_3$ or $OCF_2H$; and
(2) when $R_1$ is F or Cl, then $R_6$, $R_7$ and $R_8$ are the same as $R_1$ and Q is O or S; and when $R_1$ is H or $CH_3$, then $R_6$, $R_7$ and $R_8$ are H;

and their agriculturally suitable salts.

2. A compound of claim 1 where L is L-1.

3. A compound of claim 2 where R is H, $R_1$ is H and $R_2$ is H.

4. A compound of claim 3 where X is Cl, $CH_3$, $OCH_3$ or $OCF_2H$ and Y is $CH_3$, $OCH_3$, $OCH_2CH_3$, $CH_2OCH_3$, $CH(OCH_3)_2$ or $GCF_2T$ where G is O and T is H.

5. The compound of claim 1 which is 1,3-dihydro-N-[(4-methoxy-6-methylpyrimidin-2-yl)aminocarbonyl]-benzo[c]furan-4-sulfonamide.

6. The compound of claim 1 which is 1,3-dihydro-N-[(4,6-dimethoxypyrimidin-2-yl)aminocarbonyl]benzo[c]furan-4-sulfonamide.

7. A composition suitable for controlling the growth of undesired vegetation which comprises an effective amount of a compound of claim 1 and at least one of the following: surfactant, solid or liquid diluent.

8. A composition suitable for controlling the growth of undesired vegetation which comprises an effective amount of a compound of claim 2 and at least one of the following: surfactant, solid or liquid diluent.

9. A composition suitable for controlling the growth of undesired vegetation which comprises an effective amount of a compound of claim 3 and at least one of the following: surfactant, solid or liquid diluent.

10. A composition suitable for controlling the growth of undesired vegetation which comprises an effective amount of a compound of claim 4 and at least one of the following: surfactant, solid or liquid diluent.

11. A composition suitable for controlling the growth of undesired vegetation which comprises an effective amount of the compound of claim 5 and at least one of the following: surfactant, solid or liquid diluent.

12. A composition suitable for controlling the growth of undesired vegetation which comprises an effective amount of the compound of claim 6 and at least one of the following: surfactant, solid or liquid diluent.

13. A method for controlling the growth of undesired vegetation which comprises applying to the locus to be protected an effective amount of a compound of claim 1.

14. A method for controlling the growth of undesired vegetation which comprises applying to the locus to be protected an effective amount of a compound of claim 2.

15. A method for controlling the growth of undesired vegetation which comprises applying to the locus to be protected an effective amount of a compound of claim 3.

16. A method for controlling the growth of undesired vegetation which comprises applying to the locus to be protected an effective amount of a compound of claim 4.

17. A method for controlling the growth of undesired vegetation which comprises applying to the locus to be protected an effective amount of the compound of claim 5.

18. A method for controlling the growth of undesired vegetation which comprises applying to the locus to be protected an effective amount of the compound of claim 6.

* * * * *